(12) United States Patent
Schwarz et al.

(10) Patent No.: US 6,875,749 B2
(45) Date of Patent: *Apr. 5, 2005

(54) METHODS OF FACILITATING VASCULAR GROWTH

(75) Inventors: Margaret A. Schwarz, La Canada-Flintridge, CA (US); Fangrong Zhang, Los Angeles, CA (US); Sarah A. Gebb, Denver, CO (US)

(73) Assignees: Childrens Hospital Los Angeles, Los Angeles, CA (US); National Jewish Medical and Research Center, Denver, CO (US)

( * ) Notice: Subject to any disclaimer, the term of this patent is extended or adjusted under 35 U.S.C. 154(b) by 299 days.

This patent is subject to a terminal disclaimer.

(21) Appl. No.: 09/928,796

(22) Filed: Aug. 13, 2001

(65) Prior Publication Data

US 2002/0042086 A1 Apr. 11, 2002

Related U.S. Application Data

(63) Continuation of application No. 09/439,616, filed on Nov. 12, 1999, now Pat. No. 6,306,612.
(60) Provisional application No. 60/108,435, filed on Nov. 13, 1998.

(51) Int. Cl.[7] ............................. A61K 48/00; C12Q 1/68
(52) U.S. Cl. ........................... 514/44; 435/6; 435/325; 435/375; 536/23.1; 536/24.5
(58) Field of Search .................. 435/6, 325, 375; 536/23.1, 24.5; 514/44

(56) References Cited

U.S. PATENT DOCUMENTS 5,641,867 A    6/1997 Stern et al. ............ 530/388.23

5,885,798 A    3/1999 Bandman et al. .......... 435/69.1

FOREIGN PATENT DOCUMENTS

WO    WO 97/10841    3/1997    .......... A61K/38/17

OTHER PUBLICATIONS

Kao et al.; *Endothelial Monocyte–activating Polypeptide II, The Journal of Biological Chemistry*, 267 (28): 20239–20247 (1992).

Schwarz et al.; *EMAP II: A modulator of neovascularization in the developing lung, Am. J. Physiol*, 276: L365–L375 (1999).

Knies et al.; *Regulation of Endothelial Monocyte–Activating Polypeptide II Release by Apoptosis, Proc. Natl. Acad. Sci. USA*, 95:12322–12327 (1998).

International Search Report for PCT US99/26743; mailed Feb. 23, 2000.

Supplementary Partial European Search Report for European Patent Application Serial No. EP99958914 dated Jan. 21, 2003.

*Primary Examiner*—Sean McGarry
*Assistant Examiner*—J D Schultz
(74) *Attorney, Agent, or Firm*—Myers Bigel Sibley & Sajovec

(57) ABSTRACT

A method of facilitating vascular growth in a subject in need of such treatment comprises inhibiting EMAP II activity in the subject by an amount effective to stimulate vascular growth in the subject (e.g., in the lungs or heart of the subject). Pharmaceutical formulations useful for carrying out such methods (e.g., an antibody that specifically binds to EMAP II in a pharmaceutically acceptable carrier) and screening techniques useful for identifying additional compounds that can be used for carrying out such methods are also disclosed.

5 Claims, 11 Drawing Sheets

METHODS OF FACILITATING VASCULAR GROWTH

RELATED APPLICATIONS

This application is a continuation of U.S. application Ser. No. 09/439,616, filed Nov. 12, 1999, now issued U.S. Pat. No. 6,306,612, which claims the benefit of U.S. Provisional Application No. 60/108,435 filed Nov. 13, 1998, the disclosures of which are hereby incorporated herein in their entirety by reference.

This invention was made with Government support under Grant Numbers NIH HL-60061. The Government has certain rights to this invention.

FIELD OF THE INVENTION

The present invention concerns methods of facilitating vascular growth in a subject, such as a subject at risk for ischemic reperfusion injury, or a newborn afflicted with bronchopulmonary displaysia. Methods of identifying compounds useful for the aforesaid treatments are also disclosed.

BACKGROUND OF THE INVENTION

U.S. Pat. No. 5,641,867 to D. Stern et al. (assigned to Columbia University) describes purified endoethelial monocyte activating polypeptide (EMAP) II, antibodies that specifically bind to EMAP II, and methods of treating tumors by administering EMAP II to an afflicted subject.

U. Knies et al., *Proc. Natl. Acad. Sci. USA* 95, 12322–12327 (October 1998), describes the regulation of endothelial monocyte-activating polypepetide II release by apoptosis.

SUMMARY OF THE INVENTION

A first aspect of the invention is a method of facilitating vascular growth in a subject, such as in an organ or tissue of the subject, in need of such treatment. The method comprises inhibiting EMAP II activity in the of the subject (e.g., in the aforesaid organ or tissue) by an amount effective to stimulate vascular growth.

A second aspect of the present invention is a pharmaceutical formulation comprising: an active compound selected from the group consisting of compounds that specifically bind to EMAP II, compounds that inhibit the expression of EMAP II, and EMAP II receptor antagonists; and a pharmaceutically acceptable carrier.

A third aspect of the present invention is a method of screening for compounds useful for facilitating vascular growth in a subject in need thereof. The method comprises: contacting a test compound (e.g., a protein or peptide)to a probe molecule, the probe molecule selected from the group consisting of EMAP II and fragments thereof; and then detecting the presence or absence of binding of the test compound to the probe molecule, the presence of binding indicating the compound may be useful for facilitating vascular growth in a subject.

A fourth aspect of the present invention is a method of screening for compounds useful for facilitating vascular growth in a subject, comprising: contacting a test compound (e.g., an oligonucleotide) to probe molecule, the probe molecule selected from the group consisting of DNA encoding EMAP II, RNA encoding EMAP II, and fragments thereof; and then detecting the presence or absence of binding of the test compound to the probe molecule, the presence of binding indicating the compound may be useful for facilitating vascular growth in the subject.

A fifth aspect of the present invention is a method of screening for compounds useful for facilitating vascular growth in a subject, comprising: determining in vitro whether a test compound inhibits expression of EMAP II; the inhibition of expression of EMAP II indicating the compound may be useful for facilitating vascular growth in a subject.

The present invention is explained in greater detail in the specification set forth below.

DETAILED DESCRIPTION OF THE PREFERRED EMBODIMENTS

Figure 1:
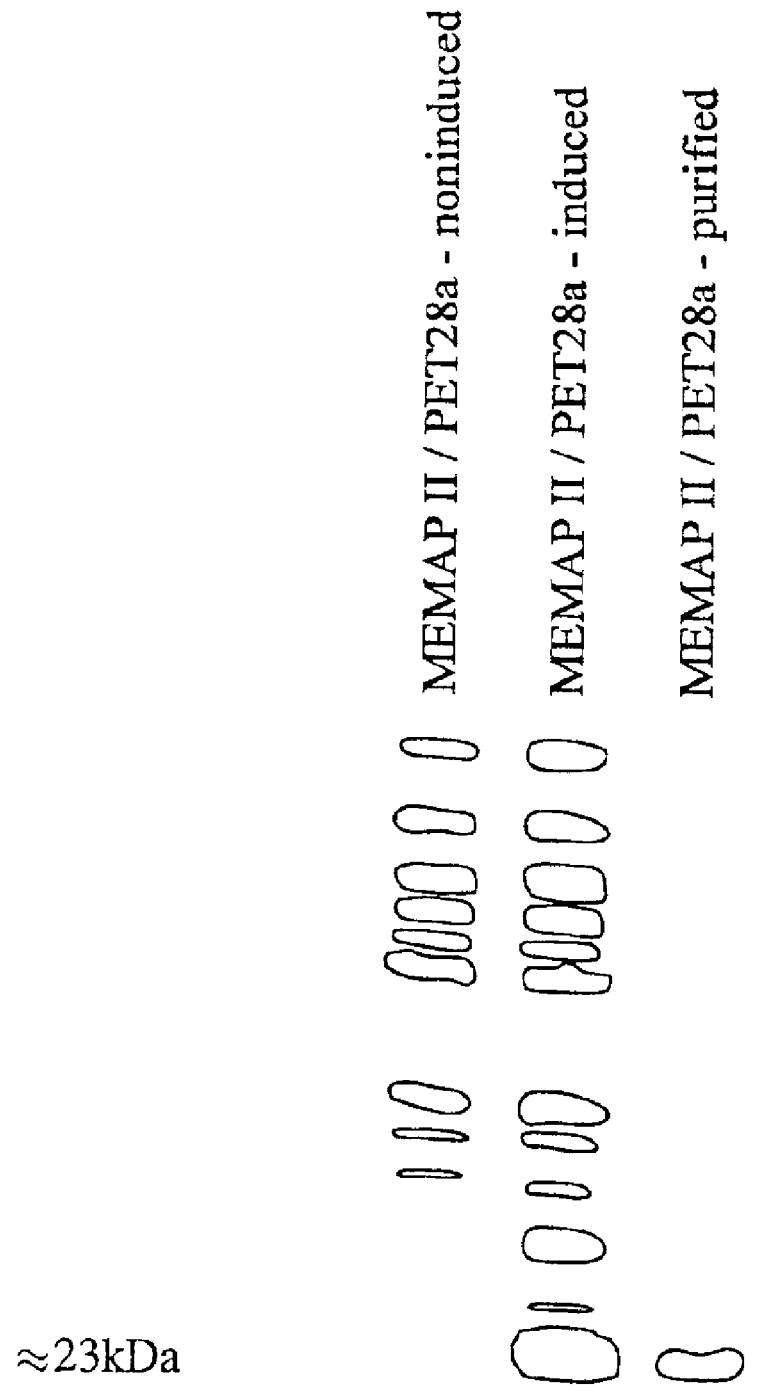
FIG. 1: Purification of recombinant (r) EMAP II. REMAP II in a PET28a 6× his-tag system was isolated after IPTG induction from *E. coli*. Lane one on this coomassie blue gel, is the initial expression of rEMAP II. Lane two represents rEMAP II induction with IPTG and purified rEMAP II in lane three.

As noted above, a first aspect of the invention is a method of facilitating vascular growth in a subject in need of such treatment. The method comprises inhibiting EMAP II activity in the subject by an amount effective to stimulate vascular growth.

Vascular growth may be inhibited in any suitable organ or tissue, including but not limited to lung, kidney, heart, aorta, gastrointestinal tract, brain, liver, etc. The inhibition may be specific or general, primarily influenced by the manner of administration as discussed below. Applicants invention is not intended to be limited to any particular theory of vascular growth, and hence this term is intended to be construed generally, encompassing any type of vascular growth such as vasculogenesis, angiogenesis, etc.

Subjects that may be treated by the present invention include any subject, human or adult, for which it is desired to facilitate vascular growth. Such subjects include subjects at risk for ischemic reperfusion injury to an organ such as those described above (e.g., in the case of transplant, low blood pressure, cardiac arrest, etc.), newborn subjects afflicted with bronchopulmonary displaysia, subjects afflicted with pulmonary hypertension, subjects afflicted with lung hypoplasia, etc.

While subjects treated by the present invention are primarily human subjects, the invention may also be carried out on other animal subjects such as dogs, cats, horses, etc. for veterinary purposes.

The inhibiting step may be carried out by any suitable means. For example, it may be carried out by administering a compound that specifically binds to EMAP II to the subject in an amount effective to stimulate vascular growth. Such compounds may be antibodies (including polyclonal and monoclonal antibodies, antibody fragments, humanized or chimeric antibodies, etc. that retain the combining region that specifically binds to EMAP II). The antibodies may be of any type of immunoglobulin, including but not limited to IgG and IgM immunoglobulins. The antibodies may be of any suitable origin, such as chicken, goat, rabbit, horse, etc., but are preferably mammalian and most preferably human. The antibody may be administered directly or through an intermediate that expresses the antibody in the subject. Examples of EMAP II antibodies are provided in U.S. Pat. No. 5,641,867 to Stern et al., the disclosure of which is incorporated herein by reference. Examples of the different forms of therapeutic antibodies are given in U.S. Pat. No. 5,622,700, the disclosure of which is incorporated herein by reference.

The inhibiting step may be carried out by downregulating EMAP II expression in the subject by an amount effective to stimulate vascular growth in the lungs of the subject. Compounds useful for downregulating EMAP II expression are, in general, antisense oligonucleotides that bind to EMAP II mRNA and disrupt translation thereof, or oligonucleotides that bind to EMAP II DNA and disrupt transcription thereof. Such oligonucleotides may be natural or synthetic (such as described in U.S. Pat. No. 5,665,593 to Kole, the disclosure of which is incorporated by reference herein in its entirety), and are typically at least 4, 6 or 8 nucleotides in length, up to the full length of the corresponding DNA or mRNA. Such oligonucleotides are selected to bind to the DNA or mRNA by Watson-Crick pairing based on the known sequence of the EMAP II DNA as described in U.S. Pat. No. 5,641,867 to Stern et al., the disclosure of which is incorporated by reference herein in its entirety. For example, an antisense oligonucleotide of the invention may consist of a 4, 6 or 8 or more nucleotide oligonucleotide having a base sequence corresponding to the EMAP II DNA sequence (SEQ ID NO: 13) disclosed in Stern et al., supra, up to 20, 30, or 40 nucleotides in length, or even the full length of the DNA sequence. In addition, such compounds may be identified in accordance with known techniques as described below.

The inhibiting step may be carried out by administering an EMAP II receptor antagonist to the subject in an amount effective to stimulate vascular growth in the lungs of the subject. EMAP II receptor antagonists may be identified in accordance with known techniques, but are in general analogs of EMAP II, such as EMAP II having three to five N-terminal and/or C-terminal amino acids deleted.

Active compounds useful for effecting the aforesaid inhibiting steps may be administered by any suitable means, including intraperitoneal, subcutaneous, intraarterial, intraveneous, intramuscular, and intrathecal injection. Injection may be through a syringe, through a canula or catheter into a desired vessel or organ, etc. The compounds may be administered by inhalation into the airways, and particularly the alveoli, of the lungs, such as by the inhalation of respirable aerosol particles (e.g., 1 to 5 micron diameter particles) comprising the active compound.

Pharmaceutical formulations of the invention typically comprise an active compound selected from the group consisting of compounds that specifically bind to EMAP II (e.g., an antibody as described above), compounds that inhibit the expression of EMAP II, and EMAP II receptor antagonists; and a pharmaceutically acceptable carrier. Any pharmaceutically acceptable carrier may be employed, such as sterile saline solution, sterile water, etc. The active compound is included in the pharmaceutically acceptable carrier in any suitable amount, such as between about 0.001, 0.005 or 0.01 percent by weight to about 10, 20 or 50 percent by weight.

Dosage of the active compound will depend upon the particular active compound, the route of administration, the particular disorder being treated, the age, weight, and condition of the subject, etc. For example, for antisense oligonucleotides, the dosage is preferably one which produces intracellular concentrations of the oligonucleotide of from 0.05 to 50 $\mu$M. typically the dosage to a human will be from about 0.01, 0.1 or 1 mg/Kg up to 50, 100, or 150 mg/Kg. In an additional example, for antibodies, the dosage is typically 0.01, 0.05 or 0.1 up to 20, 40 or 60 mg/Kg.

Active compounds that are nucleotides or proteins (e.g., antibodies) may be administered either directly as described above or through a vector intermediate that expresses the same in the subject. Thus vectors used to carry out the present invention are, in general, RNA virus or DNA virus vectors, such as lentivirus vectors, papovavirus vectors (e.g., SV40 vectors and polyoma vectors), adenovirus vectors and adeno-associated virus vectors. See generally T. Friedmann, Science 244, 1275 16 (June 1989). Examples of lentivirus vectors that may be used to carry out the present invention include Moloney Murine Leukemia Virus vectors, such as those described in U.S. Pat. No. 5,707,865 to Kohn. Any adenovirus vector can be used to carry out the present invention. See, e.g., U.S. Pat. No. 5,518,913, U.S. Pat. No. 5,670,488, U.S. Pat. No. 5,589,377; U.S. Pat. No. 5,616,326; U.S. Pat. No. 5,436,146; and U.S. Pat. No. 5,585,362. The adenovirus can be modified to alter or broaden the natural tropism thereof, as described in S. Woo, *Adenovirus redirected*, Nature Biotechnology 14, 1538 (November 1996). Any adeno-associated virus vector (or AAV vector) can also be used to carry out the present invention. See, e.g., U.S. Pat. No. 5,681,731; U.S. Pat. No. 5,677,158; U.S. Pat. No. 5,658,776; U.S. Pat. No. 5,658,776; U.S. Pat. No. 5,622,856; U.S. Pat. No. 5,604,090; U.S. Pat. No. 5,589,377; U.S. Pat. No. 5,587,308; U.S. Pat. No. 5,474,935; U.S. Pat. No. 5,436,146; U.S. Pat. No. 5,354,678; U.S. Pat. No. 5,252,479; U.S. Pat. No. 5,173,414; U.S. Pat. No. 5,139,941; and U.S. Pat. No. 4,797,368. The regulatory sequences, or the transcriptional and translational control sequences, in the vectors can be of any suitable source, so long as they effect expression of the heterologous nucleic acid in the target cells. For example, commonly used promoters are the LacZ promoter, and promoters derived from polyoma, Adenovirus 2, and Simian virus 40 (SV40). See, e.g., U.S. Pat. No. 4,599,308. The heterologous nucleic acid may encode any product that inhibits the expression of the EMAP II gene in cells infected by the vector, such as an antisense oligonucleotide that specifically binds to the EMAP II MRNA to disrupt or inhibit translation thereof, a ribozyme that specifically binds to the EMAP II mRNA to disrupt or inhibit translation thereof, or a triplex nucleic acid that specifically binds to the EMAP II duplex DNA and disrupts or inhibits transcription thereof. All of these may be carried out in accordance with known techniques, as (for example) described in U.S. Pat. Nos. 5,650,316; 5,176,996, or 5,650, 316 for triplex compounds, in U.S. Pat. Nos. 5,811,537; 5,801,154; and 5,734,039 for antisense compounds, and in U.S. Pat. Nos. 5,817,635; 5,811,300; 5,773,260; 5,766,942; 5,747,335; and 5,646,020 for ribozymes (the disclosures of which are incorporated by reference herein in their entirety). The length of the heterologous nucleic acid is not critical so long as the intended function is achieved, but the heterologous nucleic acid is typically from 5, 8, 10 or 20 nucleic acids in length up to 20, 30, 40 or 50 nucleic acids in length, up to a length equal the full length of the EMAP II gene. Once prepared, the recombinant vector can be reproduced by (a) propagating the vector in a cell culture, the cell culture comprising cells that permit the growth and reproduction of the vector therein; and then (b) collecting the recombinant vector from the cell culture, all in accordance with known techniques. The viral vectors collected from the culture may be separated from the culture medium in accordance with known techniques, and combined with a suitable pharmaceutical carrier for administration to a subject. Such pharmaceutical carriers include, but are not limited to, sterile pyrogen-free water or sterile pyrogen-free saline solution. If desired, the vectors may be packaged in liposomes for administration, in accordance with known techniques.

Any suitable route of administration can be used to carry out the present invention, depending upon the particular condition being treated. Suitable routes include, but are not limited to, intraveneous, intrarterial, intrathecal, intraperitoneal, intramuscular, and intralesional injection. Intralesional injection is currently preferred.

The dosage of the recombinant vector administered will depend upon factors such as the particular disorder, the particular vector chosen, the formulation of the vector, the condition of the patient, the route of administration, etc., and can be optimized for specific situations. In general, the dosage is from about $10^7$, $10^8$, or $10^9$ to about $10^{11}$, $10^{12}$, or $10^{13}$ plaque forming units (pfu).

In addition to their pharmaceutical or veterinary use, the recombinant vectors of the present invention (sometimes also referred to as "active agents" herein) are useful in vitro to distinguish cells in culture based on their response to the active agents, to induce apoptosis, etc. Such techniques are useful for both carrying out cell culture procedures and for drug screening purposes.

In vitro methods of screening compounds for efficacy in carrying out the methods of treatment described above are also disclosed herein. In general, in one embodiment, such methods comprise determining in vitro whether the compound inhibits the expression of EMAP II (preferably the mammalian gene, and most preferably the human gene). The inhibition of expression of EMAP II indicates the compound is useful in the methods of treatment described above. Numerous such screening methods are available. The methods can be carried out in a cell or cells, or can be carried out in essentially cell free preparation. The method can be carried out by screening for compounds that specifically disrupt either transcription or translation of EMAP II. The compound to be screened may be a member of a library of compounds (the term "compound" as used in this respect referring to both small organic compounds and other therapeutic agents such as recombinant viral vectors). The method may be carried out as a single assay, or may be implemented in the form of a high throughput screen in accordance with a variety of known techniques.

In another embodiment, the method of screening compounds comprises determining in vitro whether said compound specifically binds to EMAP II (including fragments thereof) (preferably the mammalian gene product; most preferably the human gene product). The determining step can be carried out by screening for binding of a test compound or probe molecule to the entire full length EMAP II gene product (SEQ ID NOS: 14 and 15, see Stern et al., U.S. Pat. No. 5,64,867, or to a peptide fragment thereof (e.g., a fragment of from 5, or 10 amino acids in length up to the full length of EMAP II). The binding of the compound to the EMAP II indicates that the compound is useful in the methods of treatment described herein. Such techniques can be carried out by contacting a probe compound to EMAP II or a fragment thereof in any of the variety of known combinatorial chemistry techniques (including but not limited to split pool techniques, chip-based techniques and pin-based techniques). Any suitable solid support can be used to immobilize the EMAP II or a fragment thereof to find specific binding partners thereto (or immobilize the members of the library against which the EMAP II or fragment thereof is contacted to find specific binding partners thereto), and numerous different solid supports are well known to those skilled in the art. Examples of suitable materials from which the solid support may be formed include cellulose, pore-glass, silica gel, polystyrene, particularly polystyrene cross-linked with divinylberizene, grafted copolymers such as polyethylene glycol/polystyrene, polyacrylamide, latex, dimethylacrylamide, particularly cross-linked with N,N'bis-acrylolyl ethylene diamine and comprising N-t-butoxycarbonyl-beta-alanyl-N'acrylolyl hexamethylene diamine, composites such as glass coated with a hydrophobic polymer such as cross-linked polystyrene or a fluorinated ethylene polymer to which is grafted linear polystyrene, and the like. Thus the term "solid support" includes materials conventionally considered to be semi-solid supports. General reviews of useful solid supports that include a covalently-linked reactive functionality may be found in Atherton et al., *Prospectives in Peptide Chemistry*, Karger, 101–117(1981); Amamath et al., *Chem. Rev.* 77:183 (1977); and Fridkin, The Peptides, Vol. 2, Chapter 3, Academic Press, Inc., pp 333–363 (1979). The solid support may take any suitable form, such as a bead or microparticle, a tube, a plate, a microtiter plate well, a glass microscope cover slip, etc.

The present invention can be used with probe molecules, or libraries (where groups of different probe molecules are employed), of any type. In general, such probe molecules are organic compounds, including but not limited to that may be used to carry out the present include oligomers, non-oligomers, or combinations thereof. Non-oligomers include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, benzodiazepenes, terpenes, prophyrins, toxins, catalysts, as well as combinations thereof. Oligomers include peptides (that is, oligopeptides) and proteins, oligonucleotides (the term oligonucleotide also referred to simply as "nucleotide, herein) such as DNA and RNA, oligosaccharides, polylipids, polyesters, polyamides, polyurethanes, polyureas, polyethers, poly (phosphorus derivatives) such as phosphates, phosphonates, phosphoramides, phosphonamides, phosphites, phosphinamides, etc., poly (sulfur derivatives) such as sulfones, sulfonates, sulfites, sulfonamides, sulfenamides, etc., where for the phosphorous and sulfur derivatives the indicated heteroatom for the most part will be bonded to C, H, N, O or S, and combinations thereof. Numerous methods of synthesizing or applying such probe molecules on solid supports (where the probe molecule may be either covalently or non-covalently bound to the solid support) are known, and such probe molecules can be made in accordance with procedures known to those skilled in the art. See, e.g., U.S. Pat. No. 5,565,324 to Still et al., U.S. Pat. No. 5,284,514 to Ellman et al., U.S. Pat. No. 5,445,934 to Fodor et al. (the disclosures of all United States patents cited herein are to be incorporated herein by reference in their entirety).

Test compounds used to carry out the present invention may be of any type, including both oligomers or non-oligomers of the types described above in connection with probe molecules above. Again, such test compounds are known and can be prepared in accordance with known techniques.

Where multiple different probe molecules are desired to be tested, a screening substrate useful for the high throughput screening of molecular interactions, such as in "chip-based" and "pin-based" combinatorial chemistry techniques, can be prepared in accordance with known techniques. All can be prepared in accordance with known techniques. See, e.g., U.S. Pat. No. 5,445,934 to Fodor et al., U.S. Pat. No. 5,288,514 to Ellman, and U.S. Pat. No. 5,624,711 to Sundberg et al.

In the alternative, screening of libraries of probe molecules may be carried out with mixtures of solid supports as used in "split-pool" combinatorial chemistry techniques. Such mixtures can be prepared in accordance with procedures known in the art, and tag components can be added to the discreet solid supports in accordance with procedures known in the art. See, e.g., U.S. Pat. No. 5,565,324 to Still et al.

The present invention is explained in greater detail in the following non-limiting examples.

EXAMPLE 1

EMAP II Inhibits Lung Neovascularization, Epithelial Morphogenesis and Epithelial-Mesenchymal Interactions Neovascularization is crucial to lung development and is mediated through a variety of angiogenic and anti-angiogenic factors. Herein, it is shown that excess Endothelial Monocyte Activating Polypeptide (EMAP) II, an anti-angiogenic protein, not only inhibits fetal lung neovascularization, but also significantly alters lung epithelial morphogenesis. In a murine xenograft model of lung neovascularization and morphogenesis, embryonic lungs transplanted under the skin of immunocompromised mice receiving intraperitoneal EMAP II, had a 56% reduction in vessel density ($p<0.0001$) compared to control. EMAP II treated lung transplants exhibited a marked alteration in lung morphogenesis, including lack of type II alveolar cell formation. In contrast, lung implants in animals receiving a blocking antibody to EMAP II had an increase in vessel density of 50% ($p<0.0001$) and most distal epithelial cells expressed surfactant protein C. Co-cultures of embryonic epithelial and mesenchymal cells showed that EMAP II expression is localized to the peri-epithelial cyst region. Exposure of these co-cultures to excess EMAP II inhibited epithelial cyst formation by 71% (p<0.0001); while, conversely, EMAP II antibody increased cyst formation by 54% (p<0.0001). There was a time-dependent induction of apoptosis by EMAP II limited to the epithelial cells in the co-culture system that was confirmed by apoptosis induction in the epithelial cells of the explant model. These studies demonstrate that EMAP II modulates vessel growth in the developing lung, inhibition of vessel growth, results in altered lung morphogenesis, and effects epithelial-mesenchymal interactions where, in the absence of vascular growth it induces apoptosis. Therefore, EMAP II, negatively modulates lung neovascularization as well as leading to the arrest of lung epithelial morphogenesis and apoptosis.

I. Experimental Procedures

Synthesis of Recombinant (r) EMAP II from *E. Coli* and generation of a peptide antibody. The cDNA of mature human EMAP II was cloned from RT-PCR products of U937 cells total RNA based on primers obtained from gene bank (accession #10119) into TA vector (Invitrogen). Confirmation of the clones was provided by sequence analysis, afterwhich the cDNA was inserted into PET28a, 6× his-tag containing plasmid. *E. coli*. ($DE_3$) underwent transformation with the EMAP II/PET28a plasmid and were induced with 1–4 mM IPTG. After 3–4 hours of induction, the cells were pelleted, lysed and the EMAP II protein was purified through the use of a nickel column as per protocol (Qiagen) with all procedures performed at 4° C. Briefly, pelleted cells were lysed with 50 mM $NaH_2PO_4$ pH 8.0, 300 mM NaCl, and 10 mM imidazole in the presence of lysozyme of 1 mg/ml. Following sonication, cellular debris are removed by centrifugation prior to being loaded on the Ni-NTA slurry. Following washing of the column, rEMAP II is eluted off with 8M urea, 0.1 M $NaH_2PO_4$, and 0.01 M Tris.Cl pH 5.9. Purified rEMAP II is dialyzed at 4° C. against PBS three times prior to being aliquoted and frozen at −80° C. When an aliquot of rEMAP II was thawed, it was used immediately for experiments (it was not refrozen and used in future studies). This is essential to maintain rEMAP II's activity.

A peptide sequence of 13 amino acid residues located within a homologous region of the human and murine forms of mature EMAP II were used to generate an antibody. This peptide was synthesized and the antibody produced by Zymed Laboratories Inc. as per protocol and is used for immunohistochemistry and western blotting. The antibody is specific to EMAP II identified by producing a single band on a western blot that is blocked after being incubated with excess EMAP II (data not shown).

Isolation of epithelial and mesenchymal cells for co-culture. Organotypic murine lung cultures were performed following the protocol of Schuger et al. [Schuger, *Development* 110, 1091–9 (1990); Schuger, *J. Cell. biol.* 139, 553–62 (1997); Schuger, *Int. J. Dev.Biol.* 42, 217–220 (1998)]. In brief, timed gestation 15d embryos underwent dissection from Swiss-Webster mice (Simonsen, Morgan Hill, Calif.), lungs were isolated, underwent digestion in PBS containing 0.3% trypsin and 0.1% EDTA for 10 minutes at 37° C. prior to being filtered through a 100 µm-pore mesh. The mixed epithelial-mesenchymal cells were then resuspended in minimal essential medium (MEM:Gibco-BRL) with nonessential amino acids and plated at a concentration of $2-2.5\times10^6$ cells/ml in 8 well chamber slides. Experiments were performed in the presence of vehicle, rEMAP II (mature 0.8–3.2 µg/ml), EMAP II peptide antibody (3–6 µg/ml), and rabbit IgG (control). Epithelial cyst formation was evaluated by counting the number of epithelial cyst per high power field (HPF), we analyzed 10 fields per condition and averaged them.

Xenograft lung transplant model. Timed pregnant Swiss Webster mice at gestational day 12 (based on appearance of vaginal plug=day 0) were obtained, housed, and handled according to a protocol approved by the animal care committee at CHLARI (Childrens Hospital of Los Angeles Research Institute). On day 14.5 dams were sacrificed and the embryo removed. The lungs and heart were withdrawn as a block microdissection and placed in ice cold PBS. The heart was then removed and the lung was placed on top of a 0.80 µM Millipore filter disk (Millipore) and implanted into a dorsal skinfold chamber of a nude mouse using sterile technique. The skin was closed with skin staples. A sibling lung was used for histological analysis and comparison to the implanted lung. Nude mice were then injected intraperitoneal by (IP) on a daily basis with either vehicle (phosphate buffered saline-PBS and albumin), EMAP II (1 µg/day), rabbit IgG or EMAP II antibody (25 or 50 µg/every three days).

RT-PCR of lung transplants. Following 14 days, lung xenografts were removed from mice that had been treated with rEMAP II, antibody to EMAP II, or vehicle, separated from the carrier mouse skin, total RNA was extracted by RNA STAT-60 (Tel-Test "B", Inc., Friendswood, Tex.) and the RNA of the transplanted lungs were reverse transcribed by superscript II RNase H-reverse transcriptase (GIBCO-BRL) using 3 mcg of total RNA template, 4 µl of 5× RT buffer, 2 µl of 0.1 M DTT, 0.5 µg of target gene specific 3' primer in a total reaction volume of 18 µl. The reaction mix was incubated at 70° C. for 10 minutes followed by incubation on ice 2 minutes. One µl of 10 mM dNTP, 1 µl of superscript II RNase H-reverse transcriptase were added. The mixture was incubated at 49° C. for 1 hour and 30 minutes followed by 70° C. for 10 minutes. The first strand cDNAs thus synthesized were used directly for PCR amplification of the target cDNA. The target cDNA primers were: 1) murine PECAM-1 5' primer-5' GTC ATG GCC ATG GTC GAG TA 3' (SEQ ID NO: 1) and the 3' primer-5' CTC CTC GGC ATC TTG CTG AA 3' (SEQ ID NO: 2), 2) murine tie-2 5' primer-5'TTG AAG TGA CGA ATG AGA T 3' (SEQ ID NO: 3) and the 3' primer-5' ATT TAG AGC TGT CTG GCT T 3' (SEQ ID NO: 4), 3) murine SP-C 5' primer-5'-CAT ACT GAG ATG GTC CTT GAG-3' (SEQ ID NO: 5), and 3' primer-5'-TCT GGA GCC ATC TTC ATG ATG-3' (SEQ ID NO: 6) and 4) murine T1-α 5' primer-5' GAA CAT GAG AGT ACG ACC ACT GTC AAA 3' (SEQ ID NO: 7) and the 3' primer-5' TTA GGG CGA GAA CCT TCC AGA AAT CTT 3' (SEQ ID NO: 8). β Actin, used as the house keeping gene, was performed on all the samples using the primers: 5' primer-5' GTA TGG AAT CCT GTG GCA TCC 3' (SEQ ID NO: 9) and the 3' primer-5' TAC GCA GCT CAG TAA CAG TCC 3' (SEQ ID NO: 10). In addition, controls were performed on all targeted cDNA sequences using primer pairs without the presence of the first-strand cDNA template. Target cDNA segments were amplified using ¹⁄₁₀th of the above first-strand cDNA template, 10 µl of 10× buffer, 0.5 µl of 10 mM dNTP's, 300 ng of each of 5' and 3' end specific primers, and 1 unit of Taq Polymerase (Stratagene) in a 50 µl reaction. The PCR program was 94° C. 1 min., 62° C. 30 sec., and 72° C. 30 sec. for 30 cycles. Equal amounts of all amplification cDNA fragments were analyzed by agarose gel electrophoresis, photographed, and analyzed.

In situ hybridization and construction of cDNA probes. Total RNA was extracted from 15 day gestation mouse lung tissue by RNA STAT-60 (Tel-Test "B", Inc., Friendswood, Tex.). RNA (3 µg) was incubated with oligo(dT) primer for 10 minutes at 70° C. First-strand cDNA synthesis was performed according to manufacturer's instructions (GIBCO BRL, Grand Island, N.Y.). After first-strand synthesis, cDNA was generated by PCR amplification with 10 pmol of specific primers for 30 cycles of amplification (94° C. 1', 62° C. 1', 72° C. 1'). The primers used were as follows: SP-C, sense, 5'-CAT ACT GAG ATG GTC CTT GAG-3' (SEQ ID NO: 11), and antisense, 5'-TCT GGA GCC ATC TTC ATG ATG-3' (SEQ ID NO: 12). The RNA probe for EMAP II was 456 bp in size and obtained from a region that has minimal homology with other known proteins. The generated SP-C PCR product was subcloned into TA vector (Invitrogen, Carlsbad, Calif.) for the in vitro transcription of RNA.

Digoxigenin RNA probe labeling by in vitro transcription. DNA of the SP-C subclone, in good orientation for in vitro transcription of antisense RNA by T7 RNA polymerase, was linearized by Hind III digestion and used as a template for probe labeling. Antisense RNA probe labeling with digoxigenin-UTP by in vitro transcription with T7 RNA polymerase was performed as per manufactures instructions (DIG RNA labeling kit, Boehringer Mannheim, Indianapolis, Ind.).

RNA in situ hybridization (RISH) using DIG-labeled cRNA probes. Murine embryo control lung day 14 g.a. and murine transplants, days 14 g.a.+3.5, 14 g.a.+7, 14 g.a.+ 10.5, and 14 g.a.+14 were obtained for in situ hybridization. The Dig RNA probe anti-sense and sense (control) were made using the Dig RNA labeling Kit (SP6/T7) from Boehringer Mannheim (Indianapolis, Ind.). RISH was performed on 5-mm paraffin embedded material sections according to nonradioactive in situ hybridization application manual (Boehringer Mannheim, Indianapolis, Ind.). Using DEPC treated equipment and solutions, paraffin embedded specimens underwent sectioning, rehydration and incubation in a prewarmed 5µg/ml proteinase K solution. Slides were then reimmersed in 4% PFA, treated with a 0.25% acetic anhydride and dehydrated. Sections were exposed to a hybridization solution containing 50% formamide, 10% dextran sulfate, 1 mg/ml tRNA, 1×Denhardt's solution, 4×SSC, 50mM Tris and 5mM EDTA that contained 150–300 ng/ml of dig-labeled RNA probe at 50° C. overnight. Slides were washed at 55° C. in 2×SSC/50% formamide, 1×SSC and 0.1 SSC for 30 minutes prior to being incubated with RNase A (20µg/ml) for 30 minutes at 37° C. After being rinsed with 2×SSC and Dig Nucleic Acid detection was accomplished using the Genius 3 kit from Boehringer Mannheim. Briefly, slides were incubated in 0.1 M Maleic acid/0.15 M NaCl pH 7.5 for 5 minutes after which they underwent blocking in a 1% block reagent. Following blocking, slides were incubated with anti-Dig-AP conjugate at 4° C. overnight, rinsed, and incubated with a dilute NBT/BCIP solution for 3 hours a room temperature. Slides then underwent counterstaining with a 0.02% fast green solution for 2 minutes, rinsed in water, air dried and mounted. Hybridization with sense probe or without probe was performed as negative control and they always showed no signals. All sections were examined and photographed under light microscopy.

Histologic and immunohistochemistry analysis of the murine lung transplants. Following 14 days, lung xenografts were removed from mice that had been treated with rEMAP II, blocking antibody to EMAP II, or vehicle, separated from the carrier mouse skin, fixed in 4% paraformaldehyde, dehydrated, and paraffin embedded (during all procedures, DEPC water and precaution against RNAses were taken). Fixed tissue was sectioned at 5 micron intervals. The lung transplants then underwent H & E staining for structural analysis. For immunolocalization of PECAM-1 antigens (Pharmigen, San Diego, Calif.), a rat anti-murine PECAM-1 antibody (4 µg/ml) was employed. Tissues were deparaffinized and underwent peroxide quenching. Using a histostain kit from Zymed (San Francisco, Calif.), after blocking, the sections were exposed to the primary antibody overnight at 4° C. Sections were then incubated with secondary biotinylated antibody as per the manufacturer's protocol. A brief incubation with the Streptavidin-HRP conjugate system (Zymed) was followed by development using the chromogen substrate aminoethylcarbazole. Periodic Acid Schiff (PAS) stain was performed, using a kit from Sigma (St. Louis, Mo.) according to the manufactures instructions.

TUNEL analysis of fetal epithelial-mesenchymal cell co-cultures. The spatial induction of apoptosis was analyzed in epithelial-mesenchymal cell co-culture or lung xenografts using the In Situ Death Detection Kit from Boehringer Mannheim. In brief, co-cultured cells were exposed to vehicle, EMAP II (3.2 µg/ml), EMAP II antibody (6 µg/ml) or rabbit IgG. Cells were evaluated on days one to three for apoptosis. Cells were fixed in 4% paraformaldehyde, permeabilized with 0.1% Triton-X and exposed to the TUNEL reaction (containing terminal deoxynucleotidyl transferase and a nucleotide mixture in a reaction buffer). After which, the cells were exposed to a fluorescein antibody, counterstained with propidium iodine (0.05 µg/ml), mounted with PBS/glycerol, and observed under a floursecent microscope (Olympus). Lung xenografts were fixed in 4% paraformaldehyde, dehydrated and paraffin embedded. 5 micron sections were cut, rehydrated and prior to exposure to the TUNEL reaction. Apoptotic cells were revealed using alkaline phosphatase and observed under light microscopy.

Statistics: Statistical analysis was performed using student t-test on the computer program Statview.

II. Results

Purification of recombinant EMAP II. In order to determine the function of EMAP II in the developing lung, it was important to develop an easy and reproducible production system for recombinant EMAP II. We used a PET28a 6× His-tag system to quickly and efficiently isolate mature rEMAP II under native conditions. Recombinant (r) EMAp II was expressed in *E. coli* (shown in the Coomassie blue gel, 1st column FIG. 1), induced with 1–4 mM IPTG and the *E. coli* pelleted after 3–4 hours of induction (2nd column FIG. 1). The purified, recombinant mature form of EMAP II (column 3, FIG. 1) had MR 23 kDa (with the 6× His-tag) on both reduced and nonreduced SDS-PAGE. Activity of rEMAP II, measured by induction of TNF-α and monocyte migration [Kao, 1994 #44], was found to be closely analogous to that previously observed with meth A-derived EMAP II. LPS levels were <15 pg/ml as measured with a LAL kit (Biowhittaker QCL-1000). Heat-treated EMAP II was inactive in these assays. The peptide antibody generated in a rabbit, is specific to EMAP II, identified by producing a single band on Western analysis that is blocked after being incubated with excess EMAP II (data not shown).

Figure 2:
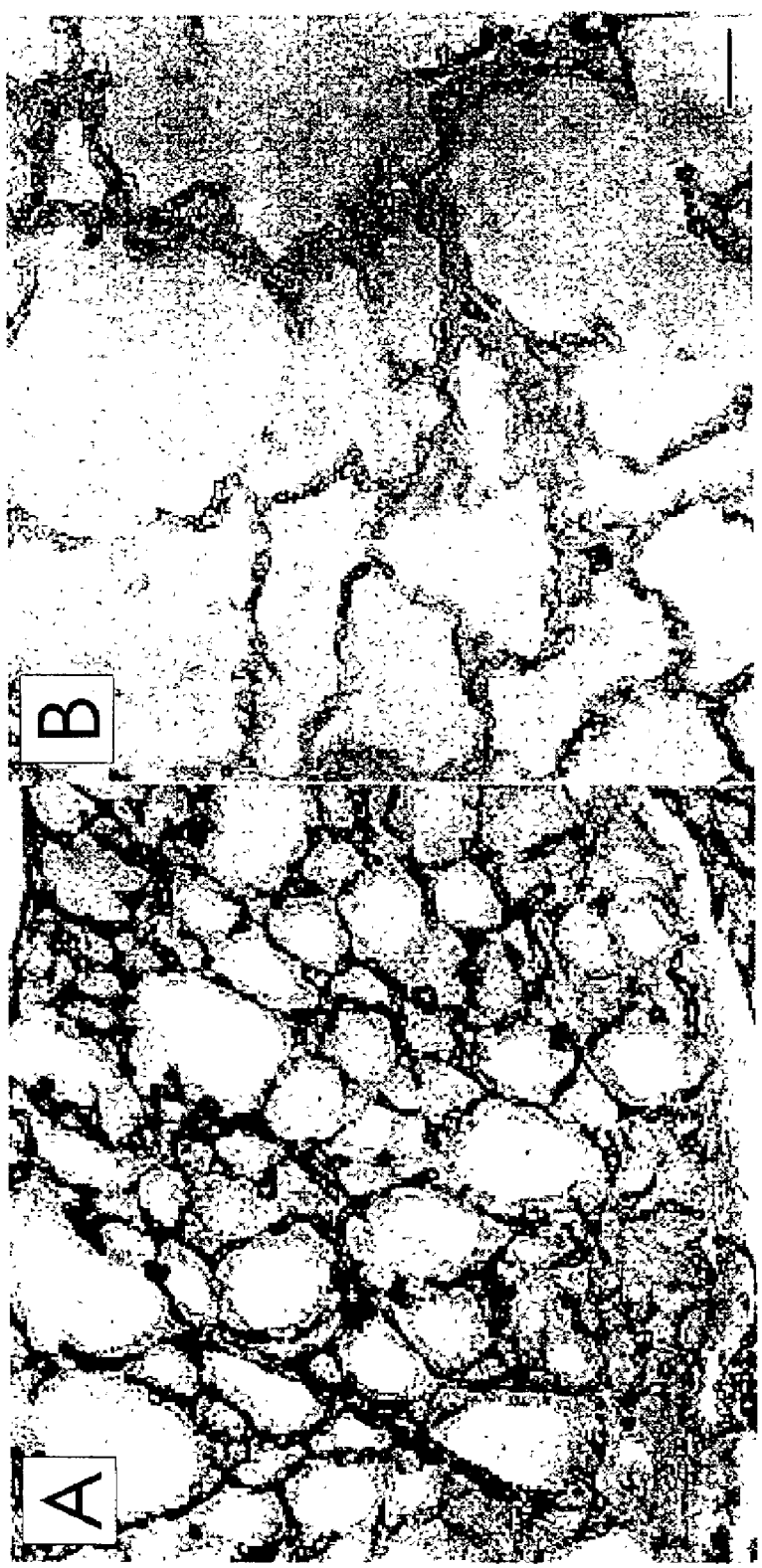
FIG. 2: EMAP II inhibits fetal lung vascular development. Fetal lung xenografts transplanted subcutaneously in immunocompromised mice treated intraperitoneally (IP) with rEMAP II, EMAP II antibody, or vehicle (PBS or rabbit serum respectively) were evaluated for vessel formation after 14 days of implantation using the PECAM-1 antibody. There was a marked inhibition of neovascularization in the transplants of mice receiving rEMAP II (2B) compared to vehicle alone (2A). Analysis of vessel formation, assessed by counting the number of vessels per HPF (averaging counts from 10 HPF per lung implant, n=20 implants/group performed on 4 separate occasions) showed a 56% reduction in neovascularization in animals receiving rEMAP II compared to control (2D) ($p<0.0001$). This is in sharp contrast to those transplants in animals that received EMAP II antibody where there is a dose dependent 50% increase in vessel counts ($p<0.0001$) (2C) compared to control (2E) (n=10/group performed on 3 separate occasions). A reduction in PECAM-1 band and Tie-2 band mRNA by RT-PCR in lung xenografts from mice treated with EMAP II and an increase in PECAM-1 and Tie-2 mRNA in animals treated with EMAP II antibody confirmed the immunohistochemical results (2F). RT-PCR results were normalized using the β-actin as an internal control. Negative controls for PCR amplification of the PECAM-1 and Tie-2. transcripts, without RT, demonstrated no specific PCR product in each rxn (data not shown). Bar=500 μm.
Figure 2C:
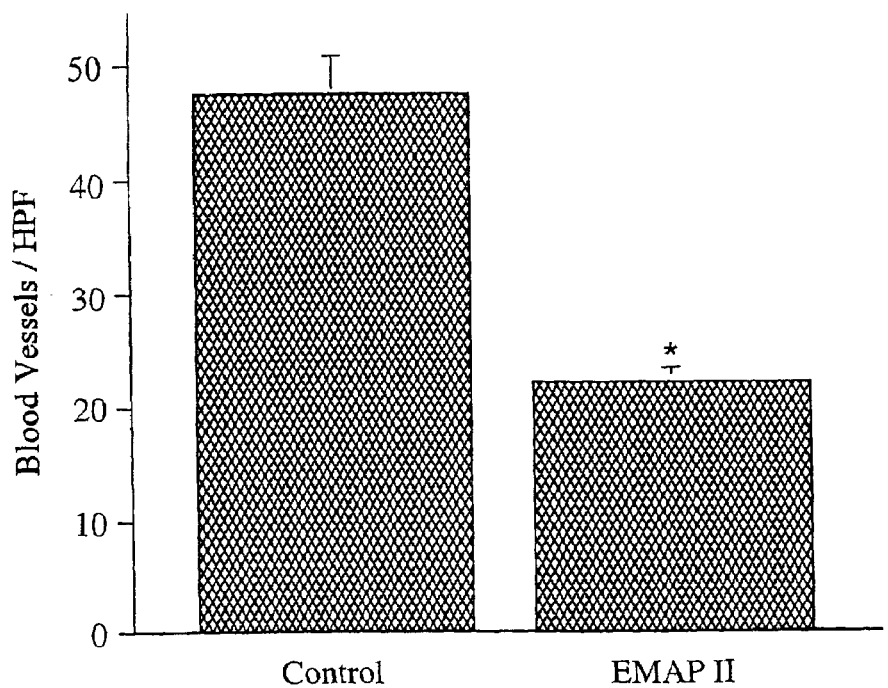
Figure 2D:
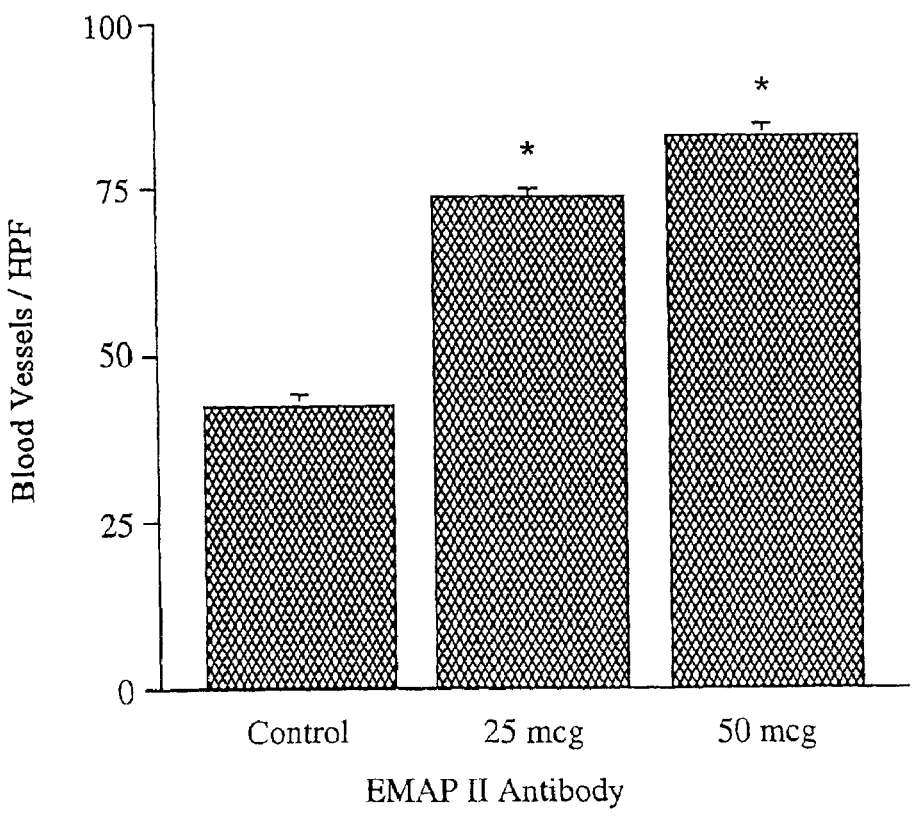
Figure 2E:
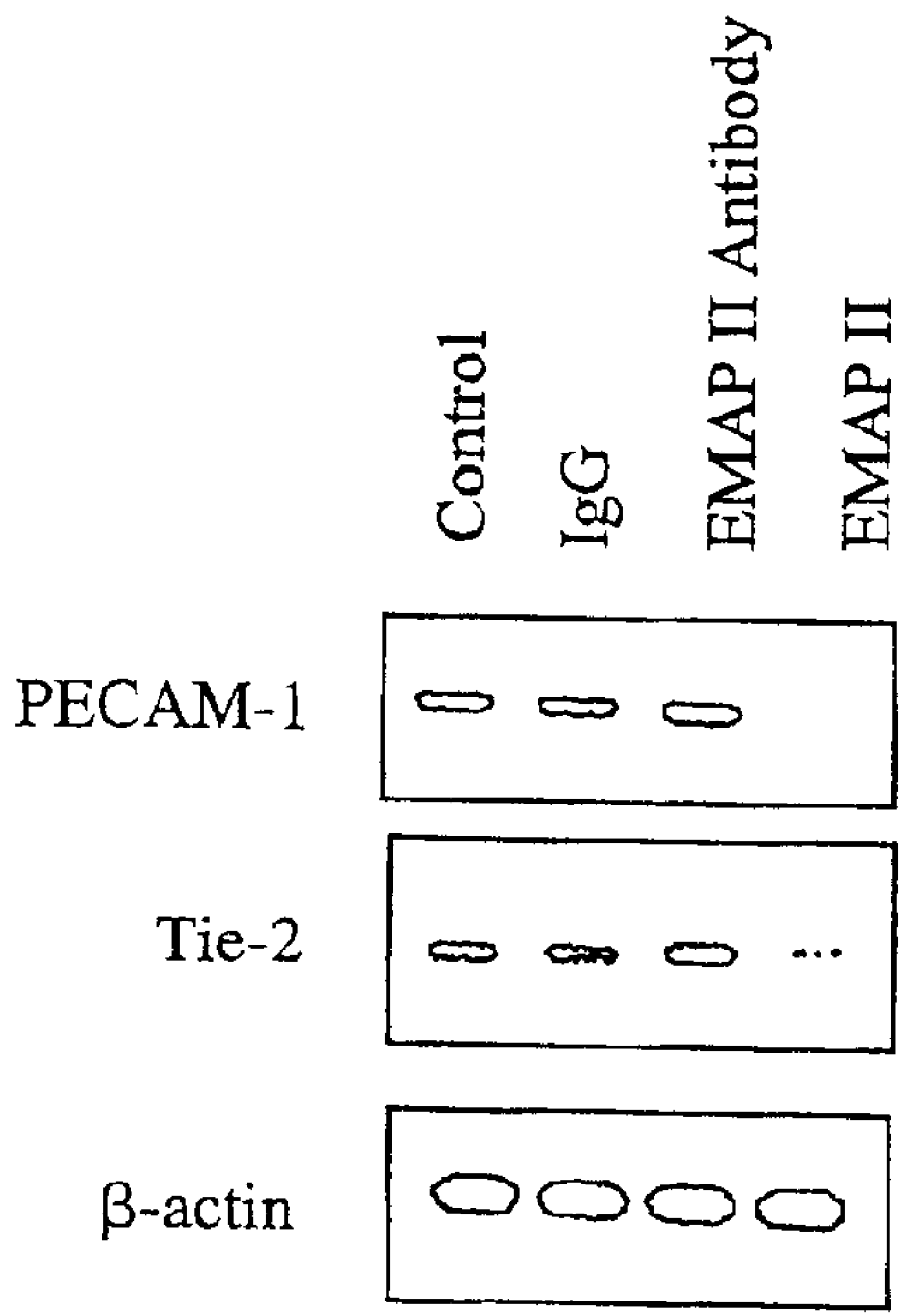

EMAP II inhibition of fetal lung vascular development. To better define EMAP II's role in embryonic lung neovascularization, murine lungs obtained at gestational age 14.5 days, were implanted subcutaneously into nude mice. Mice then received either vehicle or rEMAP II (1 μg/day) IP every day for 14 days. A separate group of mice were treated with either EMAP II blocking antibody (25 or 50 μg) or rabbit IgG every 3 days for 14 days. Lung transplants were then excised and evaluated for vascular and structural development using PECAM-1 and hematoxylin and eosin staining respectively. Compared to lung xenografts implanted in mice treated with vehicle alone, implants in mice receiving the anti-angiogenic protein EMAP II exhibited a striking 56% reduction in lung vessel formation. Differences between lung vessel formation (assessed by counting the number of vessels identified per high powered field (HPF) with PECAM-1 antibody) in control (FIG. 2A) and EMAP II treated (FIGS. 2B, D) animals were highly statistically significant by student t-test (p<0.0001). In contrast, animals receiving blocking antibody to EMAP II had a significant dose dependent increase of 50% (p<0.0001) in vessel counts per HPF (FIGS. 2C, E) (n=10/group, performed on 3 separate occasions). Consistent with these histologic findings, mRNA harvested from lung xenografts of animals treated with rEMAP II demonstrated a reduction in PECAM-1 and Tie-2 by RT-PCR compared to control. Converse results, an increase in PECAM-1 and Tie-2 PCR products, were obtained from xenografts in animals treated with the blocking EMAP II antibody (FIG. 2F). Negative controls for PCR amplification of the PECAM-1 and Tie-2 transcripts, without RT, demonstrated no specific PCR product in each rxn (data not shown).

Figure 3:
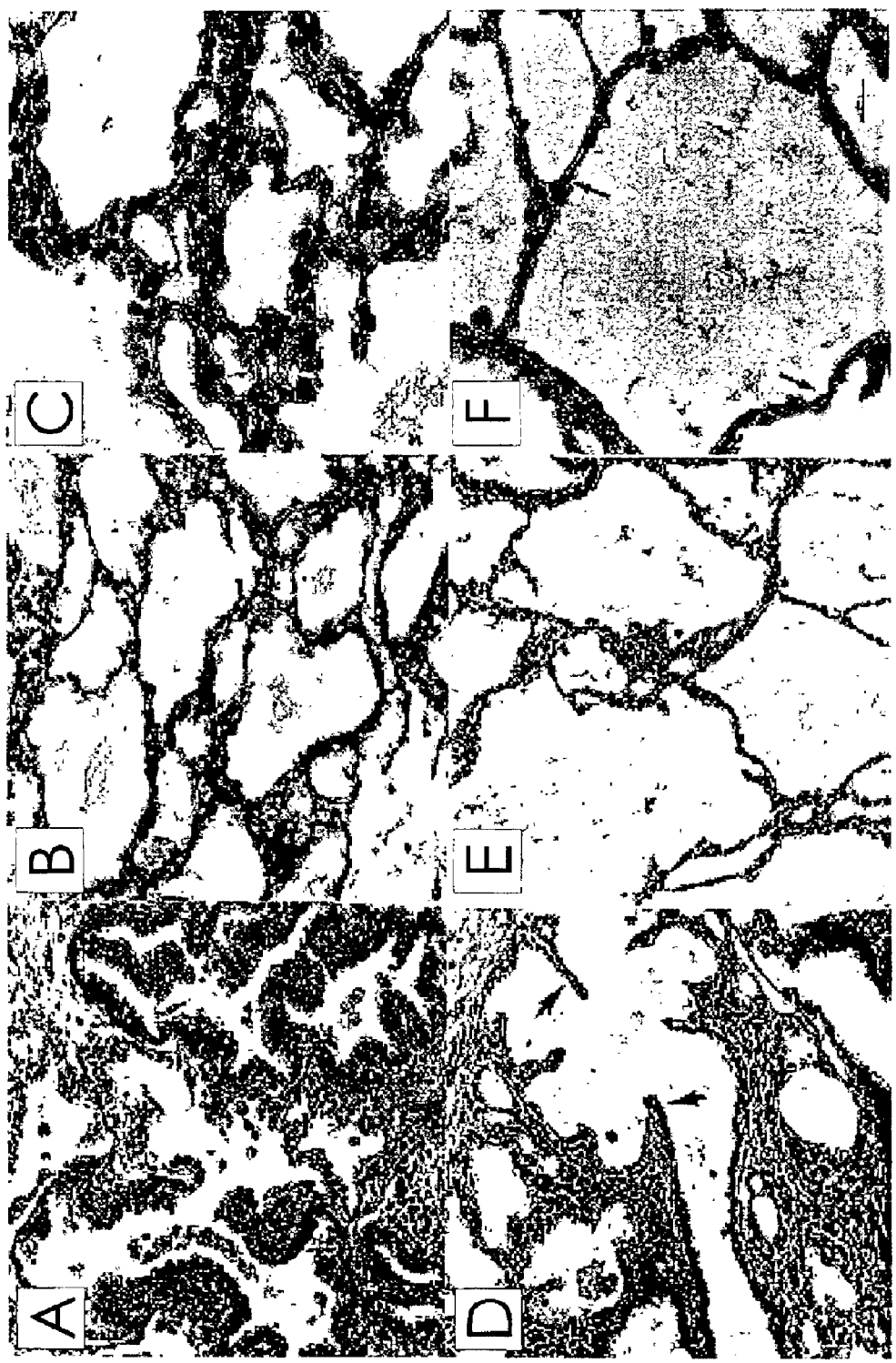
FIG. 3: Excess EMAP II leads to an alteration in lung epithelial morphogenesis. Lung xenografts in mice treated IP with rEMAP II demonstrated marked lung dysplasia, defined by the presence of flattened epithelial cells in the central airway region (arrows in 3D) and poorly formed peripheral airways (3E,F). This is in sharp contrast to those transplants in mice treated with vehicle where there were well defined bronchi, epithelium, (3A) and distal spaces with attenuated epithelium consistent with alveoli (3B,C). Bar= 500 μm in A,B,D,E; Bar=250 μm in C,F.
Figure 4:
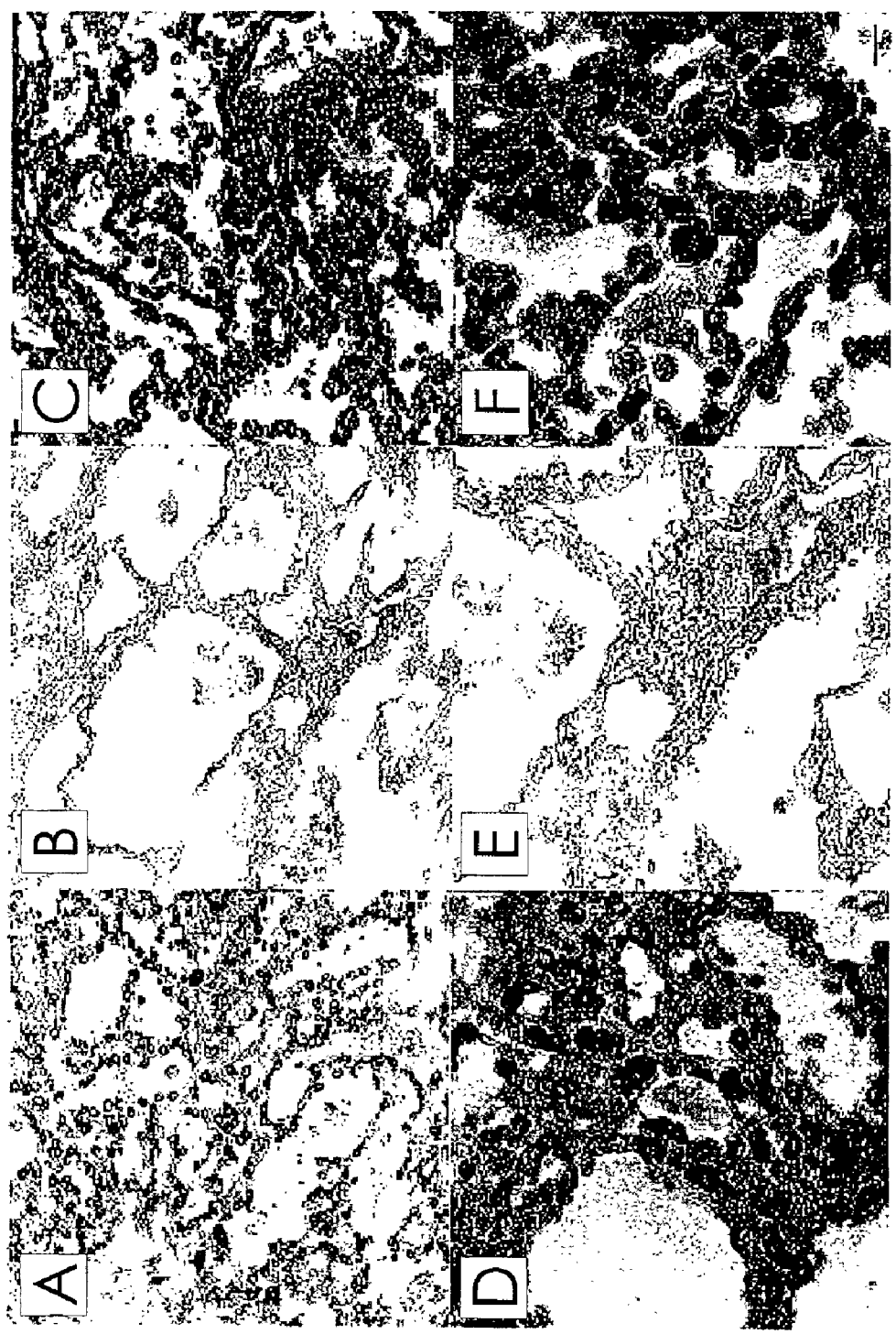
FIG. 4: Excess EMAP II significantly alters cellular differentiation in fetal lung development. Fetal lung xenografts undergo cellular differentiation with the appearance of type II alveolar cells expressing SP-C after 14 days of implantation in immunocompromised mice (4A,B) in the presence of vehicle alone. In contrast, animals receiving excess rEMAP II IP exhibit no SP-C expression throughout the entire xenograft including those areas that histologically appeared as dysplastic peripheral airways (4C,D). In contrast, an excess of type II cells is found in xenografts in animals treated with the blocking EMAP II antibody (4E,F). This is indicative of a marked effect of EMAP II on lung epithelial maturation. These in situ hybridization findings were supported by a reduction in SP-C RNA in lung xenografts from mice treated with EMAP II compared to control and an increase in animals treated with EMAP II antibody (4G). Assessment of type I alveolar cell markers revealed a slight elevation in T1-α in xenografts treated with rEMAP II compared to control. There was also a marked reduction of T1-α in xenografts in animals treated with the blocking EMAP II, the inverse of the high level of in situ hybridization of SP-C in type II cells (4G). RT-PCR results were normalized using the housekeeping gene β-actin (350 bp). Negative controls, demonstrated no band (data not shown). Bar=500 μm in A,C,E; 250 μm in B,D,F.

EMAP II inhibits epithelial maturation. It was postulated that pulmonary vascularization might influence epithelial cell differentiation. After administration of rEMAP II, histologic analysis of lung xenografts in these mice showed a marked inhibition of structural maturation (FIGS. 3D–F) compared to vehicle treated animals (FIGS. 3A–C). This was demonstrated by a lack of well-defined bronchi with characteristic epithelium (FIG. 3A), or of distal airways with attenuated epithelium consistent with alveolar epithelium, as compared to those xenografts where the mouse received vehicle alone (FIGS. 3B,C). In addition, lung xenografts in mice treated with EMAP II had alveolar epithelial cells that appeared dysplastic (FIGS. 3E,F) and an apparent stasis in respiratory duct formation (FIG. 3D, arrows) as compared to those transplants in mice receiving vehicle alone (3A). To discern whether morphologic progression actually occurred, we assessed the xenografts for markers of distal lung morphogenesis. Lung xenografts in mice receiving vehicle alone underwent type II alveolar cell differentiation as marked by SP-C expression (FIGS. 4A,B). In contrast, lung xenografts in animals receiving EMAP II had a marked reduction in SP-C expression throughout the entire transplanted lung, even in the most peripheral airways (FIGS. 4C,D) Further supporting our findings, animals receiving blocking EMAP II antibody had a strikingly increased number of type II cells, with essentially every distal epithelial cell expressing SP-C (FIGS. 4E,F). Therefore, it appeared that excess EMAP II lead to profound inhibition of peripheral lung epithelial morphogenesis and differentiation.

Figure 4G:
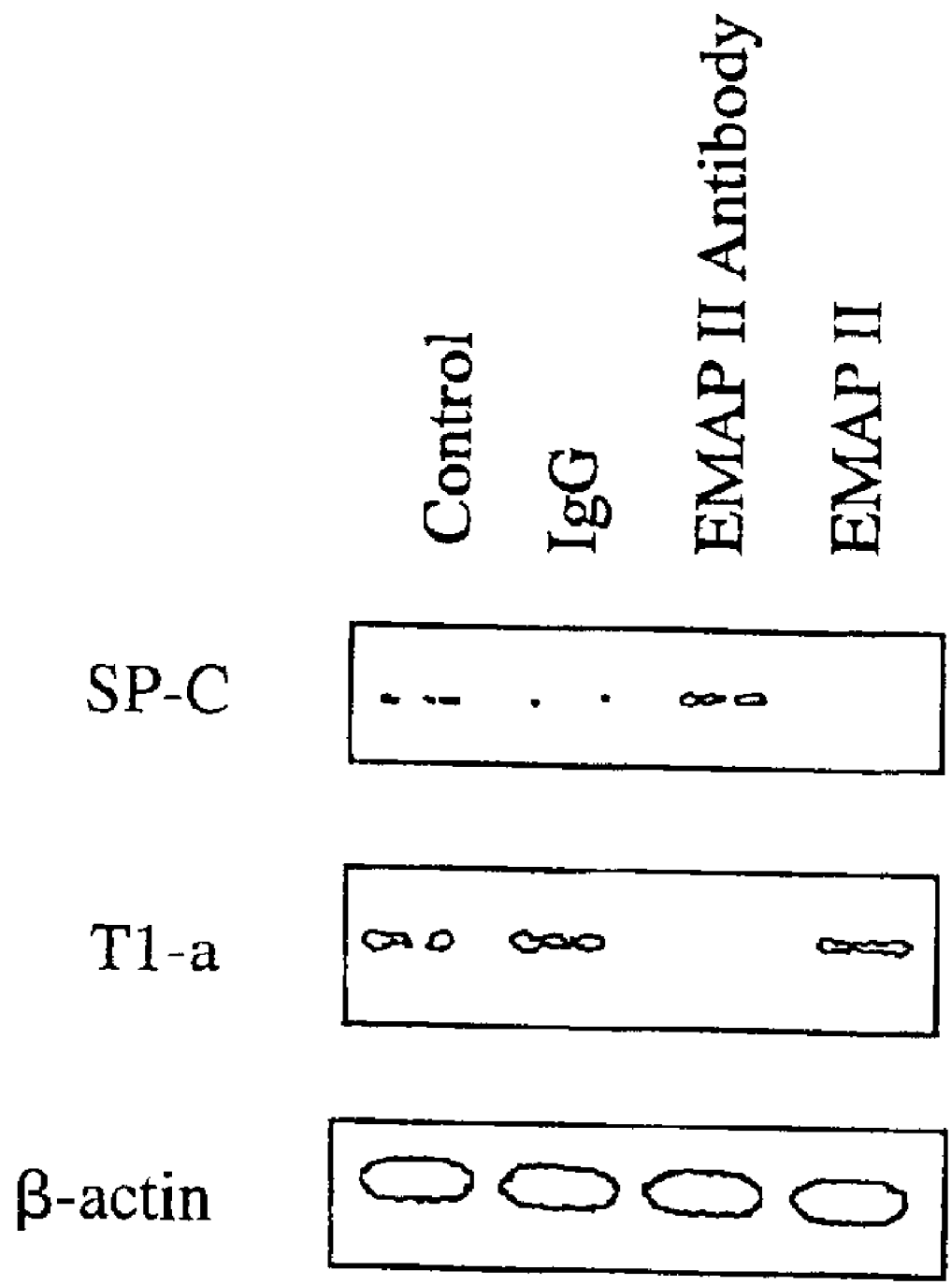

Consistent with the in situ hybridization findings, mRNA harvested from lung xenografts of animals treated with rEMAP II demonstrated a reduction in SP-C by RT-PCR compared to controls. In contrast, animals treated with the blocking EMAP II antibody exhibited an increase in the SP-C amplicon confirming the in situ results (FIG. 4G). Interestingly, T1-α type I alveolar epithelial cell marker, was slightly elevated in xenografts treated with rEMAP II, whereas a marked reduction in T1-α was found in the blocking EMAP II antibody treated lungs, the inverse of the high level of SP-C expression, a type II cell marker (FIG. 4G). Negative controls for PCR amplification of the SP-C and T1-α transcripts, without RT, demonstrated no specific PCR product in each rxn (data not shown).

Figure 5:
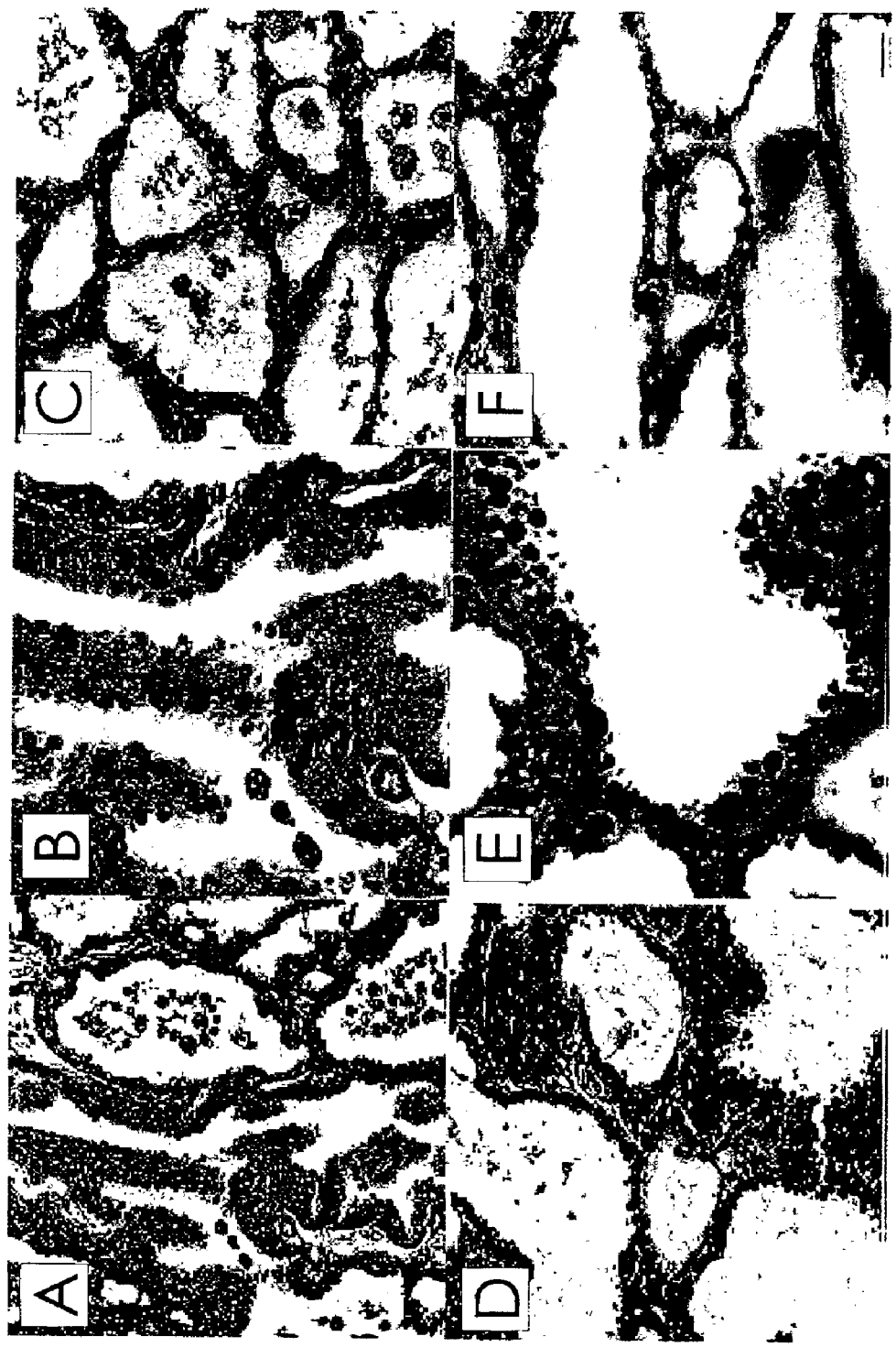
FIG. 5: Effect of excess rEMAP II on glycogen within the xenografts. Glycogen (denoted as the magenta color of the PAS stain) is markedly elevated in those lung transplants in mice treated IP with rEMAP II (5D–F). In contrast, xenografts in vehicle treated mice contain a normal distribution of glycogen, consistent with that seen in the late saccular stage (5A–C). Thus, presence of excess EMAP II appears to halt lung formation in the glycogen-rich epithelial stage, associated with the beginning of the canalicular (vascular) stage, just prior to alveolar type II epithelial cell differentiation. Bar=500 μm in A,B,D,E; 250 μm C,F.

We also evaluated glycogen production in the lung xenografts. Xenografts obtained from mice treated with rEMAP II demonstrated excess glycogen production (denoted by the magenta color) (FIGS. 5D–F) compared to vehicle alone (FIGS. 5A–C), further supporting the concept that EMAP II inhibited epithelial differentiation.

Figure 6:
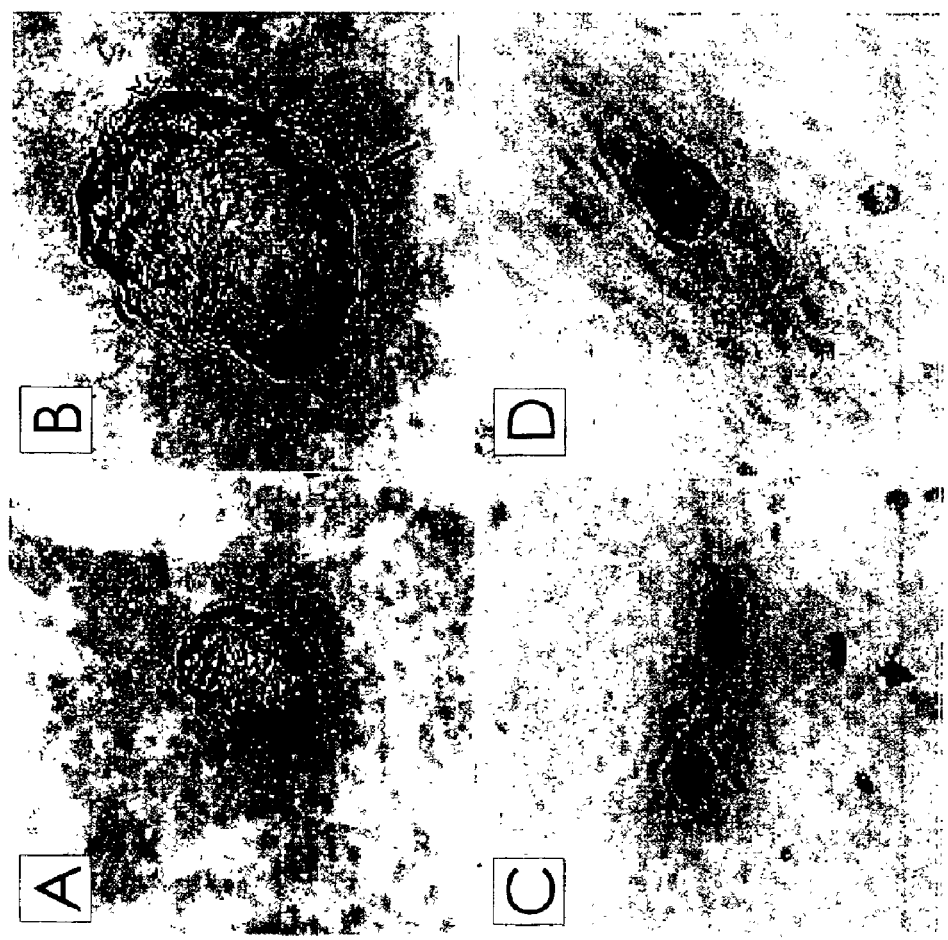
FIG. 6: In situ hybridization of EMAP II exhibits a peri-epithelial cyst pattern of EMAP II expression (6A) that is confirmed by immunohistochemistry (6B). In contrast to minimal production of EMAP II in the distal mesenchyme, the mesenchymal cells in close contact with the epithelium display a marked increase in EMAP II as indicated by the arrows in 6B. Therefore, it appears that in addition to expression of EMAP II in the epithelial and mesenchymal cells, it is the actual cell-cell interaction between the epithelial and mesenchymal cells that increases EMAP II's expression. Bar=500 μm in A,C; 250 μm in B,D.

EMAP II disruption of the epithelial-mesenchymal interface. To further examine the role of the anti-angiogenic protein EMAP II in lung morphogenesis, the localization of EMAP II in epithelial-mesenchymal co-cultures was defined. Evaluation of lung epithelial-mesenchymal co-cultures after 3 days of incubation revealed EMAP II expression to be predominately in the peri-epithelial cyst region by both in situ hybridization (FIG. 6A) as well as immunohistochemistry (FIG. 6B) consistent with those results seen in fetal lung tissue [Schwarz, Am. J. Physiol. 276, L365–75 (1999)]. Interestingly, while EMAP II is expressed in epithelial and mesenchymal cells, its strongest expression is noted to be at the epithelial-mesenchymal junction as noted by the arrows in FIG. 6A.

Figure 7:
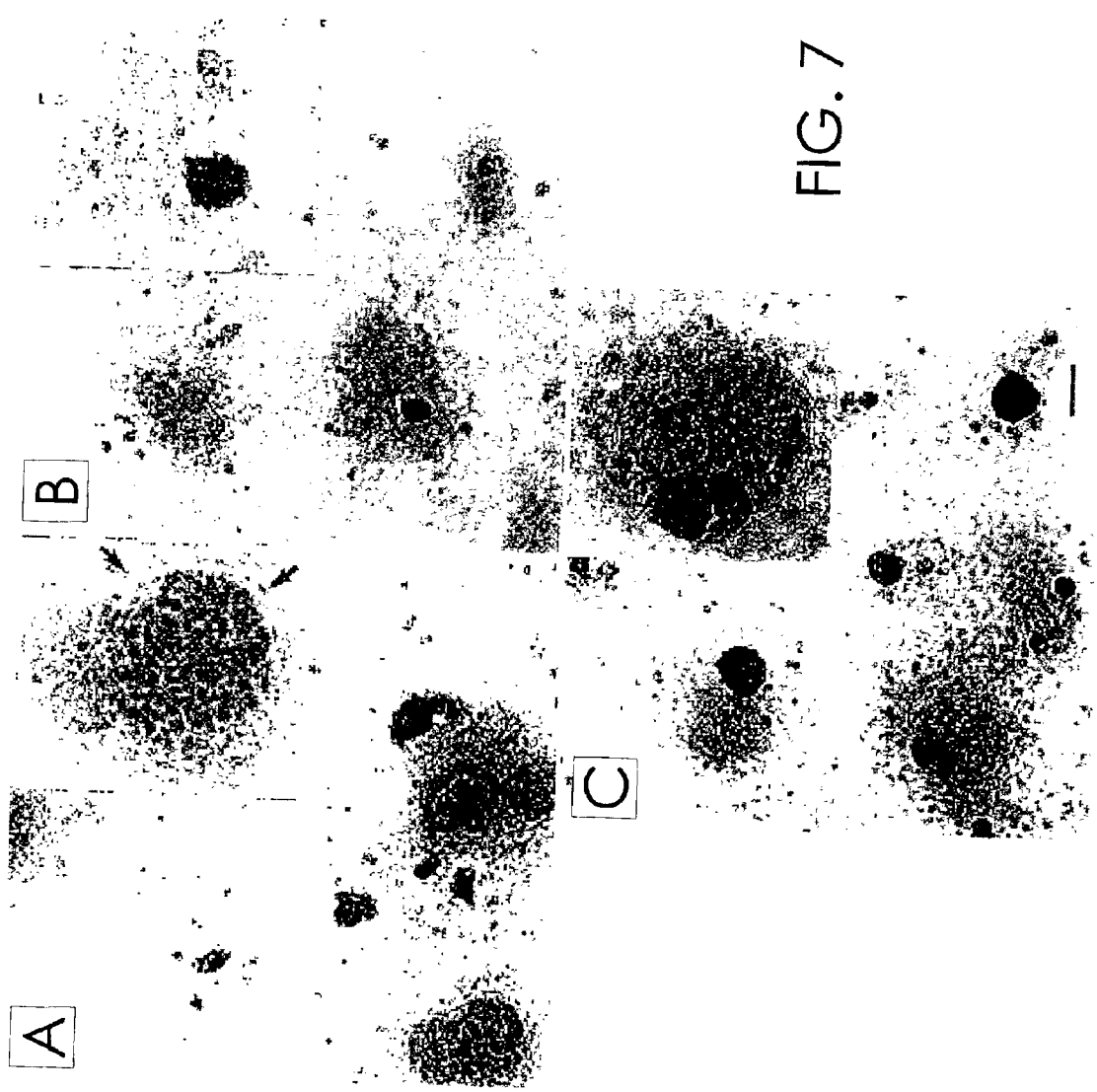
FIG. 7: Effect of EMAP II on epithelial cyst formation in co-cultures. Co-cultures of epithelial and mesenchymal cells exposed to excess rEMAP II have a marked 71% decrease of epithelial cyst formation (7B) in a dose-dependent fashion (7D) as compared to vehicle alone (7A). In addition, in contrast to normal cyst formation noted in the inset of FIG. 7A, where the cyst is enclosed by a flattened cell population (arrows in 7A inset) consistent with the laminin cell population surrounding the cyst, those co-cultures treated with EMAP II (7B, inset) or EMAP II antibody (7C, inset) lacked the normal cyst formation. In contrast, co-cultures grown in the presence of EMAP II antibody reflect a 54% increase in cyst formation (7C) that is also dose-dependent in nature (7E). We speculate that excess EMAP II interferes with epithelial cyst formation and stability. (n=7/group performed on 4 different occasions) Bar=500 μm in A–C; 250 μm insets of A–C.
Figure 7D:
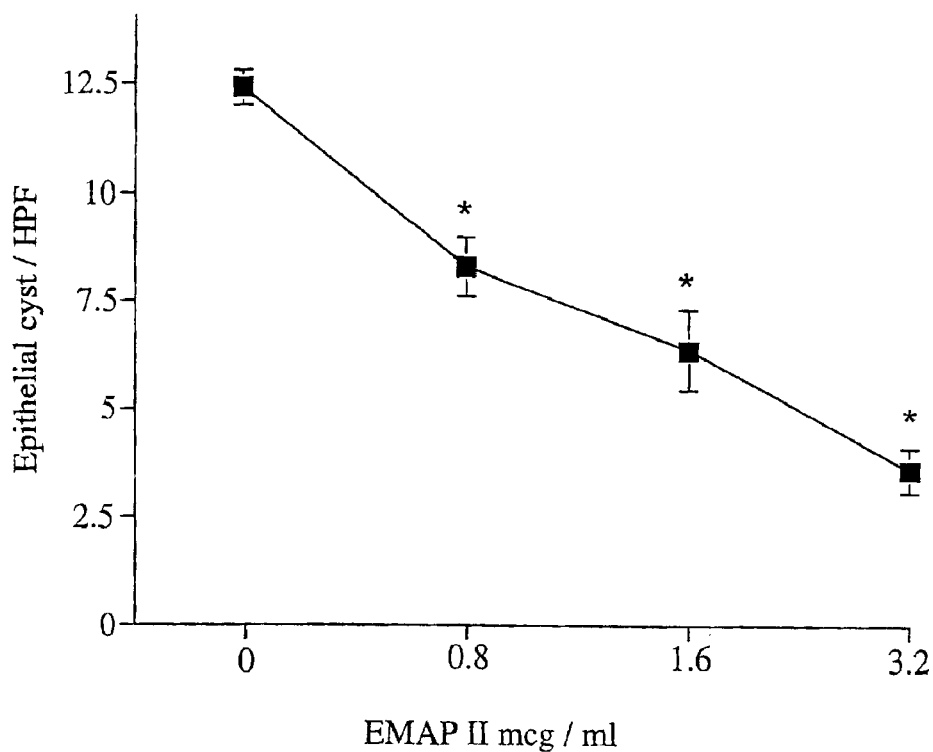
Figure 7E:
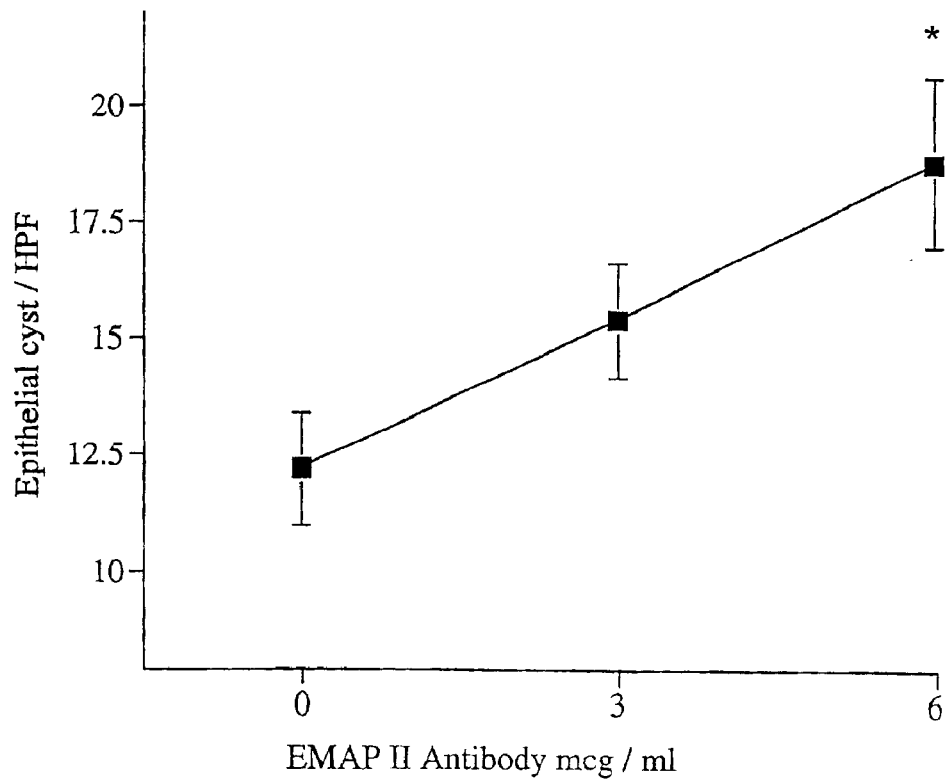

To determine the effect of EMAP II on epithelial cyst formation, epithelial-mesenchymal co-cultures were exposed to increasing concentrations of rEMAP II, EMAP II blocking antibody, or vehicle (PBS or rabbit IgG respectively). Epithelial cyst formation was analyzed as the total number of cyst formed per high power field (HPF). There was a dose-dependent, 71% inhibition (p<0.0001) of epithelial cyst formation and an alteration in structure in co-cultures exposed to EMAP II (FIGS. 7B, D) as compared to control (FIG. 7A, arrows indicate normal epithelial cyst formation with the epithelial cells being surrounded by flattened laminin positive cells). Conversely, in the presence of the EMAP II blocking antibody (FIG. 7C, E) there was a 54% increase (p<0.01) in cyst formation that was also dose-dependent. Because we recently observed that EMAP II induces apoptosis in growing and dividing endothelial cells [Schwarz, Journal. of Experimental. Medicine 290 (1999)], we employed the TUNEL assay to determine whether induction of apoptosis due by EMAP II was responsible for the decrease in numbers of epithelial cyst. We found a time-dependent induction of apoptosis, starting in the peri-epithelial cyst region and progressing to include the entire epithelial cyst in co-cultures treated with rEMAP II as compared to control (data not shown). Apoptosis was also markedly decreased in those cultures exposed to the EMAP II blocking antibody as compared to control (data not shown). Consistent with our findings in vitro, lung xenografts in animals treated with EMAP II had a marked increase in apoptosis localizing to the epithelial cells (data not shown).

The foregoing is illustrative of the present invention, and is not to be construed as limiting thereof. The invention is defined by the following claims, with equivalents of the claims to be included therein.

That which is claimed is:

1. A method of screening for compounds useful for facilitating vascular growth in a subject, comprising:
   determining in vitro whether a test compound inhibits expression of an EMAP II of SEQ ID NO: 14 or 15;
   the inhibition of expression of the EMAP II of SEQ ID NO: 14 or 15 indicating said compound may be useful for facilitating vascular growth in a subject.

2. The method according to claim 1, wherein said determining step is carried out in a cell.

3. The method according to claim 1, wherein said determining step comprises determining whether said compound inhibits transcription of a nucleic acid encoding an EMAP II of SEQ ID NO: 14 or 15.

4. The method according to claim 1, wherein said determining step comprises determining whether said compound inhibits translation of a nucleic acid encoding an EMAP II of SEQ ID NO: 14 or 15.

5. The method according to claim 1, wherein said determining step is carried out in a cell-free preparation.

* * * * *

UNITED STATES PATENT AND TRADEMARK OFFICE
CERTIFICATE OF CORRECTION

PATENT NO. : 6,875,749 B2
DATED : April 5, 2005
INVENTOR(S) : Schwarz et al.

Page 1 of 1

It is certified that error appears in the above-identified patent and that said Letters Patent is hereby corrected as shown below:

Column 7,
Line 15, should read -- U.S. Patent No. 5,641,867, or to a peptide fragment thereof (e.g., --.

Signed and Sealed this

Thirtieth Day of August, 2005

JON W. DUDAS
*Director of the United States Patent and Trademark Office*

SEQUENCE LISTING

<160> NUMBER OF SEQ ID NOS: 15

<210> SEQ ID NO 1
<211> LENGTH: 20
<212> TYPE: DNA
<213> ORGANISM: Artificial
<220> FEATURE:
<223> OTHER INFORMATION: Oligonucleotide primer

<400> SEQUENCE: 1
gtcatggcca tggtcgagta                                               20

<210> SEQ ID NO 2
<211> LENGTH: 20
<212> TYPE: DNA
<213> ORGANISM: Artificial
<220> FEATURE:
<223> OTHER INFORMATION: Oligonucleotide primer

<400> SEQUENCE: 2
ctcctcggca tcttgctgaa                                               20

<210> SEQ ID NO 3
<211> LENGTH: 19
<212> TYPE: DNA
<213> ORGANISM: Artificial
<220> FEATURE:
<223> OTHER INFORMATION: Oligonucleotide primer

<400> SEQUENCE: 3
ttgaagtgac gaatgagat                                                19

<210> SEQ ID NO 4
<211> LENGTH: 19
<212> TYPE: DNA
<213> ORGANISM: Artificial
<220> FEATURE:
<223> OTHER INFORMATION: Oligonucleotide primer

<400> SEQUENCE: 4
atttagagct gtctggctt                                                19

<210> SEQ ID NO 5
<211> LENGTH: 21
<212> TYPE: DNA
<213> ORGANISM: Artificial
<220> FEATURE:
<223> OTHER INFORMATION: Oligonucleotide primer

<400> SEQUENCE: 5
catactgaga tggtccttga g                                             21

<210> SEQ ID NO 6
<211> LENGTH: 21
<212> TYPE: DNA
<213> ORGANISM: Artificial
<220> FEATURE:
<223> OTHER INFORMATION: Oligonucleotide primer

<400> SEQUENCE: 6
tctggagcca tattcatgat g                                             21

<210> SEQ ID NO 7
<211> LENGTH: 27

```
<212> TYPE: DNA
<213> ORGANISM: Artificial
<220> FEATURE:
<223> OTHER INFORMATION: Oligonucleotide primer

<400> SEQUENCE: 7
gaacatgaga gtacgaccac tgtcaaa                                           27

<210> SEQ ID NO 8
<211> LENGTH: 27
<212> TYPE: DNA
<213> ORGANISM: Artificial
<220> FEATURE:
<223> OTHER INFORMATION: Oligonucleotide primer

<400> SEQUENCE: 8
ttagggcgag aaccttccag aaatctt                                           27

<210> SEQ ID NO 9
<211> LENGTH: 21
<212> TYPE: DNA
<213> ORGANISM: Artificial
<220> FEATURE:
<223> OTHER INFORMATION: Oligonucleotide primer

<400> SEQUENCE: 9
gtatggaatc ctgtggcatc c                                                 21

<210> SEQ ID NO 10
<211> LENGTH: 21
<212> TYPE: DNA
<213> ORGANISM: Artificial
<220> FEATURE:
<223> OTHER INFORMATION: Oligonucleotide primer

<400> SEQUENCE: 10
tacgcagctc agtaacagtc c                                                 21

<210> SEQ ID NO 11
<211> LENGTH: 21
<212> TYPE: DNA
<213> ORGANISM: Artificial
<220> FEATURE:
<223> OTHER INFORMATION: Oligonucleotide primer

<400> SEQUENCE: 11
catactgaga tggtccttga g                                                 21

<210> SEQ ID NO 12
<211> LENGTH: 21
<212> TYPE: DNA
<213> ORGANISM: Artificial
<220> FEATURE:
<223> OTHER INFORMATION: Oligonucleotide primer

<400> SEQUENCE: 12
tctggagcca tcttcatgat g                                                 21

<210> SEQ ID NO 13
<211> LENGTH: 1086
<212> TYPE: DNA
<213> ORGANISM: Mus musculus
<220> FEATURE:
<221> NAME/KEY: CDS
<222> LOCATION: (64)..(993)

<400> SEQUENCE: 13
```

-continued

| | |
|---|---|
| gaggctgctc aagagctgcg gttgggtcac cgcttcatgt ttctctgccg attctgggga | 60 |

| | | | | | | | | | | | | | | | | |
|---|---|---|---|---|---|---|---|---|---|---|---|---|---|---|---|---|
| aag | atg | gca | acg | aat | gat | gct | gtt | ctg | aag | agg | ctg | gag | cag | aag | ggt | 108 |
| | Met | Ala | Thr | Asn | Asp | Ala | Val | Leu | Lys | Arg | Leu | Glu | Gln | Lys | Gly | |
| | 1 | | | 5 | | | | | 10 | | | | | 15 | | |

| | | | | | | | | | | | | | | | |
|---|---|---|---|---|---|---|---|---|---|---|---|---|---|---|---|
| gca | gag | gcg | gat | cag | atc | atc | gaa | tat | ctc | aag | cag | cag | gtt | gct | ctt | 156 |
| Ala | Glu | Ala | Asp | Gln | Ile | Ile | Glu | Tyr | Leu | Lys | Gln | Gln | Val | Ala | Leu | |
| | | | 20 | | | | | 25 | | | | | 30 | | | |

| | | | | | | | | | | | | | | | |
|---|---|---|---|---|---|---|---|---|---|---|---|---|---|---|---|
| ctt | aag | gag | aaa | gca | att | ttg | cag | gca | aca | atg | aga | gaa | gaa | aag | aaa | 204 |
| Leu | Lys | Glu | Lys | Ala | Ile | Leu | Gln | Ala | Thr | Met | Arg | Glu | Glu | Lys | Lys | |
| | | 35 | | | | | 40 | | | | | 45 | | | | |

| | | | | | | | | | | | | | | | |
|---|---|---|---|---|---|---|---|---|---|---|---|---|---|---|---|
| ctt | cga | gtt | gaa | aat | gct | aaa | ctg | aaa | aaa | gaa | ata | gaa | gag | cta | aag | 252 |
| Leu | Arg | Val | Glu | Asn | Ala | Lys | Leu | Lys | Lys | Glu | Ile | Glu | Glu | Leu | Lys | |
| | | 50 | | | | | 55 | | | | | 60 | | | | |

| | | | | | | | | | | | | | | | |
|---|---|---|---|---|---|---|---|---|---|---|---|---|---|---|---|
| caa | gag | ctg | att | ctg | gca | gaa | att | cat | aac | gga | gtg | gag | caa | gtg | cgt | 300 |
| Gln | Glu | Leu | Ile | Leu | Ala | Glu | Ile | His | Asn | Gly | Val | Glu | Gln | Val | Arg | |
| | 65 | | | | | 70 | | | | | 75 | | | | | |

| | | | | | | | | | | | | | | | |
|---|---|---|---|---|---|---|---|---|---|---|---|---|---|---|---|
| gtt | cga | ttg | agt | act | cca | ctg | cag | acg | aac | tgt | act | gct | tct | gaa | agt | 348 |
| Val | Arg | Leu | Ser | Thr | Pro | Leu | Gln | Thr | Asn | Cys | Thr | Ala | Ser | Glu | Ser | |
| 80 | | | | | 85 | | | | | 90 | | | | | 95 | |

| | | | | | | | | | | | | | | | |
|---|---|---|---|---|---|---|---|---|---|---|---|---|---|---|---|
| gtg | gtg | cag | tct | cca | tca | gta | gca | acc | acc | gcc | tct | cct | gct | aca | aaa | 396 |
| Val | Val | Gln | Ser | Pro | Ser | Val | Ala | Thr | Thr | Ala | Ser | Pro | Ala | Thr | Lys | |
| | | | 100 | | | | | 105 | | | | | 110 | | | |

| | | | | | | | | | | | | | | | |
|---|---|---|---|---|---|---|---|---|---|---|---|---|---|---|---|
| gag | cag | atc | aaa | gcg | gga | gaa | gaa | aag | aag | gtg | aaa | gag | aag | act | gaa | 444 |
| Glu | Gln | Ile | Lys | Ala | Gly | Glu | Glu | Lys | Lys | Val | Lys | Glu | Lys | Thr | Glu | |
| | | | 115 | | | | | 120 | | | | | 125 | | | |

| | | | | | | | | | | | | | | | |
|---|---|---|---|---|---|---|---|---|---|---|---|---|---|---|---|
| aag | aaa | gga | gag | aaa | aag | gag | aag | cag | cag | tcg | gca | gca | gca | agt | act | 492 |
| Lys | Lys | Gly | Glu | Lys | Lys | Glu | Lys | Gln | Gln | Ser | Ala | Ala | Ala | Ser | Thr | |
| | | 130 | | | | | 135 | | | | | 140 | | | | |

| | | | | | | | | | | | | | | | |
|---|---|---|---|---|---|---|---|---|---|---|---|---|---|---|---|
| gac | tcc | aag | cct | atc | gac | gca | tcg | cgt | ctg | gat | ctt | cga | att | ggt | tgt | 540 |
| Asp | Ser | Lys | Pro | Ile | Asp | Ala | Ser | Arg | Leu | Asp | Leu | Arg | Ile | Gly | Cys | |
| | | 145 | | | | | 150 | | | | | 155 | | | | |

| | | | | | | | | | | | | | | | |
|---|---|---|---|---|---|---|---|---|---|---|---|---|---|---|---|
| att | gtt | act | gcc | aag | aag | cac | cct | gat | gca | gat | tca | ctg | tat | gtg | gag | 588 |
| Ile | Val | Thr | Ala | Lys | Lys | His | Pro | Asp | Ala | Asp | Ser | Leu | Tyr | Val | Glu | |
| 160 | | | | | 165 | | | | | 170 | | | | | 175 | |

| | | | | | | | | | | | | | | | |
|---|---|---|---|---|---|---|---|---|---|---|---|---|---|---|---|
| gaa | gta | gat | gtg | gga | gaa | gca | gcc | ccg | cgc | acg | gtc | gtc | agc | ggg | ctg | 636 |
| Glu | Val | Asp | Val | Gly | Glu | Ala | Ala | Pro | Arg | Thr | Val | Val | Ser | Gly | Leu | |
| | | | | 180 | | | | | 185 | | | | | 190 | | |

| | | | | | | | | | | | | | | | |
|---|---|---|---|---|---|---|---|---|---|---|---|---|---|---|---|
| gtg | aat | cat | gtt | cct | cta | gaa | cag | atg | caa | aat | cgt | atg | gtg | gtt | tta | 684 |
| Val | Asn | His | Val | Pro | Leu | Glu | Gln | Met | Gln | Asn | Arg | Met | Val | Val | Leu | |
| | | | 195 | | | | | 200 | | | | | 205 | | | |

| | | | | | | | | | | | | | | | |
|---|---|---|---|---|---|---|---|---|---|---|---|---|---|---|---|
| ctc | tgt | aat | ctg | aag | cct | gca | aag | atg | cgg | gga | gtt | ctg | tct | caa | gcc | 732 |
| Leu | Cys | Asn | Leu | Lys | Pro | Ala | Lys | Met | Arg | Gly | Val | Leu | Ser | Gln | Ala | |
| | | | 210 | | | | | 215 | | | | | 220 | | | |

| | | | | | | | | | | | | | | | |
|---|---|---|---|---|---|---|---|---|---|---|---|---|---|---|---|
| atg | gtg | atg | tgt | gcc | agt | tca | cca | gag | aaa | gtg | gag | att | ctg | gcc | cct | 780 |
| Met | Val | Met | Cys | Ala | Ser | Ser | Pro | Glu | Lys | Val | Glu | Ile | Leu | Ala | Pro | |
| | 225 | | | | | 230 | | | | | 235 | | | | | |

| | | | | | | | | | | | | | | | |
|---|---|---|---|---|---|---|---|---|---|---|---|---|---|---|---|
| ccc | aac | ggg | tcc | gtt | cct | ggg | gac | aga | att | act | ttt | gat | gct | ttt | cct | 828 |
| Pro | Asn | Gly | Ser | Val | Pro | Gly | Asp | Arg | Ile | Thr | Phe | Asp | Ala | Phe | Pro | |
| 240 | | | | | 245 | | | | | 250 | | | | | 255 | |

| | | | | | | | | | | | | | | | |
|---|---|---|---|---|---|---|---|---|---|---|---|---|---|---|---|
| gga | gag | cct | gac | aag | gag | cta | aac | cct | aag | aag | aag | atc | tgg | gag | cag | 876 |
| Gly | Glu | Pro | Asp | Lys | Glu | Leu | Asn | Pro | Lys | Lys | Lys | Ile | Trp | Glu | Gln | |
| | | | | 260 | | | | | 265 | | | | | 270 | | |

| | | | | | | | | | | | | | | | |
|---|---|---|---|---|---|---|---|---|---|---|---|---|---|---|---|
| atc | cag | cct | gac | ctg | cac | acc | aat | gct | gag | tgt | gtg | gcc | aca | tac | aaa | 924 |
| Ile | Gln | Pro | Asp | Leu | His | Thr | Asn | Ala | Glu | Cys | Val | Ala | Thr | Tyr | Lys | |
| | | | | 275 | | | | | 280 | | | | | 285 | | |

| | | | | | | | | | | | | | | | |
|---|---|---|---|---|---|---|---|---|---|---|---|---|---|---|---|
| gga | gct | ccc | ttt | gag | gtg | aag | ggg | aag | gga | gtt | tgc | aga | gcc | caa | acc | 972 |
| Gly | Ala | Pro | Phe | Glu | Val | Lys | Gly | Lys | Gly | Val | Cys | Arg | Ala | Gln | Thr | |
| | | 290 | | | | | 295 | | | | | 300 | | | | |

-continued

```
atg gcc aat agt gga att aaa taagtgctct gtaactgaaa gacattggcg      1023
Met Ala Asn Ser Gly Ile Lys
    305             310 aaaacttaat aacaataaag agaagtgtgt ttatcactta catataaaaa aaaaaaaaa   1083 aaa                                                                1086
```

<210> SEQ ID NO 14
<211> LENGTH: 310
<212> TYPE: PRT
<213> ORGANISM: Mus musculus

<400> SEQUENCE: 14

```
Met Ala Thr Asn Asp Ala Val Leu Lys Arg Leu Glu Gln Lys Gly Ala
1               5                   10                  15

Glu Ala Asp Gln Ile Ile Glu Tyr Leu Lys Gln Val Ala Leu Leu
                20                  25                  30

Lys Glu Lys Ala Ile Leu Gln Ala Thr Met Arg Glu Glu Lys Lys Leu
            35                  40                  45

Arg Val Glu Asn Ala Lys Leu Lys Lys Glu Ile Glu Glu Leu Lys Gln
        50                  55                  60

Glu Leu Ile Leu Ala Glu Ile His Asn Gly Val Gln Val Arg Val
65                  70                  75                  80

Arg Leu Ser Thr Pro Leu Gln Thr Asn Cys Thr Ala Ser Glu Ser Val
                85                  90                  95

Val Gln Ser Pro Ser Val Ala Thr Thr Ala Ser Pro Ala Thr Lys Glu
            100                 105                 110

Gln Ile Lys Ala Gly Glu Glu Lys Val Lys Glu Lys Thr Glu Lys
        115                 120                 125

Lys Gly Glu Lys Lys Glu Lys Gln Gln Ser Ala Ala Ser Thr Asp
    130                 135                 140

Ser Lys Pro Ile Asp Ala Ser Arg Leu Asp Leu Arg Ile Gly Cys Ile
145                 150                 155                 160

Val Thr Ala Lys Lys His Pro Asp Ala Asp Ser Leu Tyr Val Glu Glu
                165                 170                 175

Val Asp Val Gly Glu Ala Ala Pro Arg Thr Val Val Ser Gly Leu Val
            180                 185                 190

Asn His Val Pro Leu Glu Gln Met Gln Asn Arg Met Val Val Leu Leu
        195                 200                 205

Cys Asn Leu Lys Pro Ala Lys Met Arg Gly Val Leu Ser Gln Ala Met
    210                 215                 220

Val Met Cys Ala Ser Ser Pro Glu Lys Val Glu Ile Leu Ala Pro Pro
225                 230                 235                 240

Asn Gly Ser Val Pro Gly Asp Arg Ile Thr Phe Asp Ala Phe Pro Gly
                245                 250                 255

Glu Pro Asp Lys Glu Leu Asn Pro Lys Lys Ile Trp Glu Gln Ile
            260                 265                 270

Gln Pro Asp Leu His Thr Asn Ala Glu Cys Val Ala Thr Tyr Lys Gly
        275                 280                 285

Ala Pro Phe Glu Val Lys Gly Lys Gly Val Cys Arg Ala Gln Thr Met
    290                 295                 300

Ala Asn Ser Gly Ile Lys
305             310
```

<210> SEQ ID NO 15
<211> LENGTH: 312

-continued

```
<212> TYPE: PRT
<213> ORGANISM: Homo sapiens

<400> SEQUENCE: 15

Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
            20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Ala Phe
65                  70                  75                  80

Pro Ser Gly Thr Pro Leu His Ala Asn Ser Met Val Ser Glu Asn Val
                85                  90                  95

Ile Gln Ser Thr Ala Val Thr Thr Val Ser Ser Gly Thr Lys Glu Gln
            100                 105                 110

Ile Lys Gly Gly Thr Gly Asp Glu Lys Lys Ala Lys Glu Lys Ile Glu
        115                 120                 125

Lys Lys Gly Glu Lys Lys Glu Lys Lys Gln Gln Ser Ile Ala Gly Ser
    130                 135                 140

Ala Asp Ser Lys Pro Ile Asp Val Ser Arg Leu Asp Leu Arg Ile Gly
145                 150                 155                 160

Cys Ile Ile Thr Ala Arg Lys His Pro Asp Ala Asp Ser Leu Tyr Val
                165                 170                 175

Glu Glu Val Asp Val Gly Glu Ile Ala Pro Arg Thr Val Val Ser Gly
            180                 185                 190

Leu Val Asn His Val Pro Leu Glu Gln Met Gln Asn Arg Met Val Ile
        195                 200                 205

Leu Leu Cys Asn Leu Lys Pro Ala Lys Met Arg Gly Val Leu Ser Gln
    210                 215                 220

Ala Met Val Met Cys Ala Ser Ser Pro Glu Lys Ile Glu Ile Leu Ala
225                 230                 235                 240

Pro Pro Asn Gly Ser Val Pro Gly Asp Arg Ile Thr Phe Asp Ala Phe
                245                 250                 255

Pro Gly Glu Pro Asp Lys Glu Leu Asn Pro Lys Lys Lys Ile Trp Glu
            260                 265                 270

Gln Ile Gln Pro Asp Leu His Thr Asn Asp Glu Cys Val Ala Thr Tyr
        275                 280                 285

Lys Gly Val Pro Phe Glu Val Lys Gly Lys Gly Val Cys Arg Ala Gln
    290                 295                 300

Thr Met Ser Asn Ser Gly Ile Lys
305                 310
```